(12) United States Patent
Trivett et al.

(10) Patent No.: US 10,410,848 B2
(45) Date of Patent: *Sep. 10, 2019

(54) PROBE ADAPTOR ASSEMBLY

(71) Applicant: Micromass UK Limited, Wilmslow, Cheshire (GB)

(72) Inventors: Ian Trivett, Cheadle (GB); Stephen O'Brien, Manchester (GB); Graeme Dutton, Burnely (GB)

(73) Assignee: MICROMASS UK LIMITED, Wilmslow (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/947,609

(22) Filed: Apr. 6, 2018

(65) Prior Publication Data

US 2018/0226239 A1    Aug. 9, 2018

Related U.S. Application Data

(63) Continuation of application No. 15/464,924, filed on Mar. 21, 2017, now Pat. No. 9,947,522.

(30) Foreign Application Priority Data

Nov. 4, 2016  (GB) .................................. 1606123.6
Nov. 4, 2016  (GB) .................................. 1606124.4

(51) Int. Cl.
*H01J 49/04*  (2006.01)
*G01N 30/72*  (2006.01)
(Continued)

(52) U.S. Cl.
CPC .......... *H01J 49/0404* (2013.01); *F16L 15/08* (2013.01); *G01N 30/7233* (2013.01);
(Continued)

(58) Field of Classification Search
CPC .............. H01J 49/0404; H01J 49/0422; G01N 30/7233
(Continued)

(56) References Cited

U.S. PATENT DOCUMENTS

| 4,641,541 A | 2/1987 | Sharp |
| 5,175,433 A | 12/1992 | Browner et al. |

(Continued)

FOREIGN PATENT DOCUMENTS

| GB | 2548596 A | 9/2017 |
| JP | 2009294086 A | 12/2009 |
| WO | 2013/063502 A2 | 5/2013 |

OTHER PUBLICATIONS

Herring et al., "An On-Line Preconcentrator and the Evaluation of Electrospray Interfaces for the Capillary Electrophoresis/Mass Spectrometry of Peptides", Rapid Communications in Mass Spectrometry, vol. 13, No. 1, pp. 1-7, 1999.
(Continued)

*Primary Examiner* — Nicole M Ippolito
*Assistant Examiner* — Hanway Chang
(74) *Attorney, Agent, or Firm* — Womble Bond Dickinson (US) LLP; Deborah M. Vernon; Heath T. Misley

(57) ABSTRACT

An apparatus for connecting an ionization probe assembly to a mass and/or ion mobility spectrometer is disclosed. The apparatus comprises: an attachment member for releasably attaching a probe assembly to the apparatus; a cap for enclosing the attachment member; wherein the apparatus is operable to deliver a voltage to a probe assembly only when the cap is arranged to enclose the attachment member; and wherein the cap is configurable to enclose the attachment member when a probe assembly is attached to the apparatus.

20 Claims, 30 Drawing Sheets

(51) Int. Cl.
 F16L 15/08 (2006.01)
 G01N 27/62 (2006.01)
(52) U.S. Cl.
 CPC ........ *H01J 49/0422* (2013.01); *G01N 27/622* (2013.01); *G01N 30/7266* (2013.01)
(58) Field of Classification Search
 USPC .................. 250/428, 430; 850/52, 53, 56, 63
 See application file for complete search history.

(56) References Cited

U.S. PATENT DOCUMENTS

| | | | |
|---|---|---|---|
| 6,753,521 | B1 | 6/2004 | Park et al. |
| 7,075,066 | B2 | 7/2006 | Bailey et al. |
| 7,960,711 | B1 | 6/2011 | Sheehan et al. |
| 8,227,750 | B1 | 7/2012 | Zhu et al. |
| 8,384,026 | B2 | 2/2013 | O'Malley et al. |
| 8,723,109 | B2 | 5/2014 | Newton |
| 8,759,758 | B2 | 6/2014 | Steiner et al. |
| 9,188,569 | B2 | 11/2015 | Graham |
| 9,459,240 | B2 | 10/2016 | Vorm |
| 2005/0023455 | A1 | 2/2005 | Bailey et al. |
| 2005/0061673 | A1 | 3/2005 | Presto Elgstoen et al. |
| 2011/0180706 | A1 | 7/2011 | O'Malley et al. |
| 2014/0305801 | A1 | 10/2014 | Peterson et al. |
| 2016/0217992 | A1 | 7/2016 | O'Brien et al. |

OTHER PUBLICATIONS

Jackson et al., "Electrical Equivalence of Electrospray Ionization with Conducting and Nonconducting Needles", Analytical Chemistry, vol. 71, No. 17, pp. 3777-3784, 1999.

Kertesz et al., "Minimizing Analyte Electrolysis in an Electrospray Emitter", Journal of Mass Spectrometry, vol. 36, No. 2, pp. 204-210, 2001.

Combined Search and Examination Report issed by the Intellectual Property Office of the United Kingdom relating to Application No. GB1806438.6, dated Aug. 31, 2018.

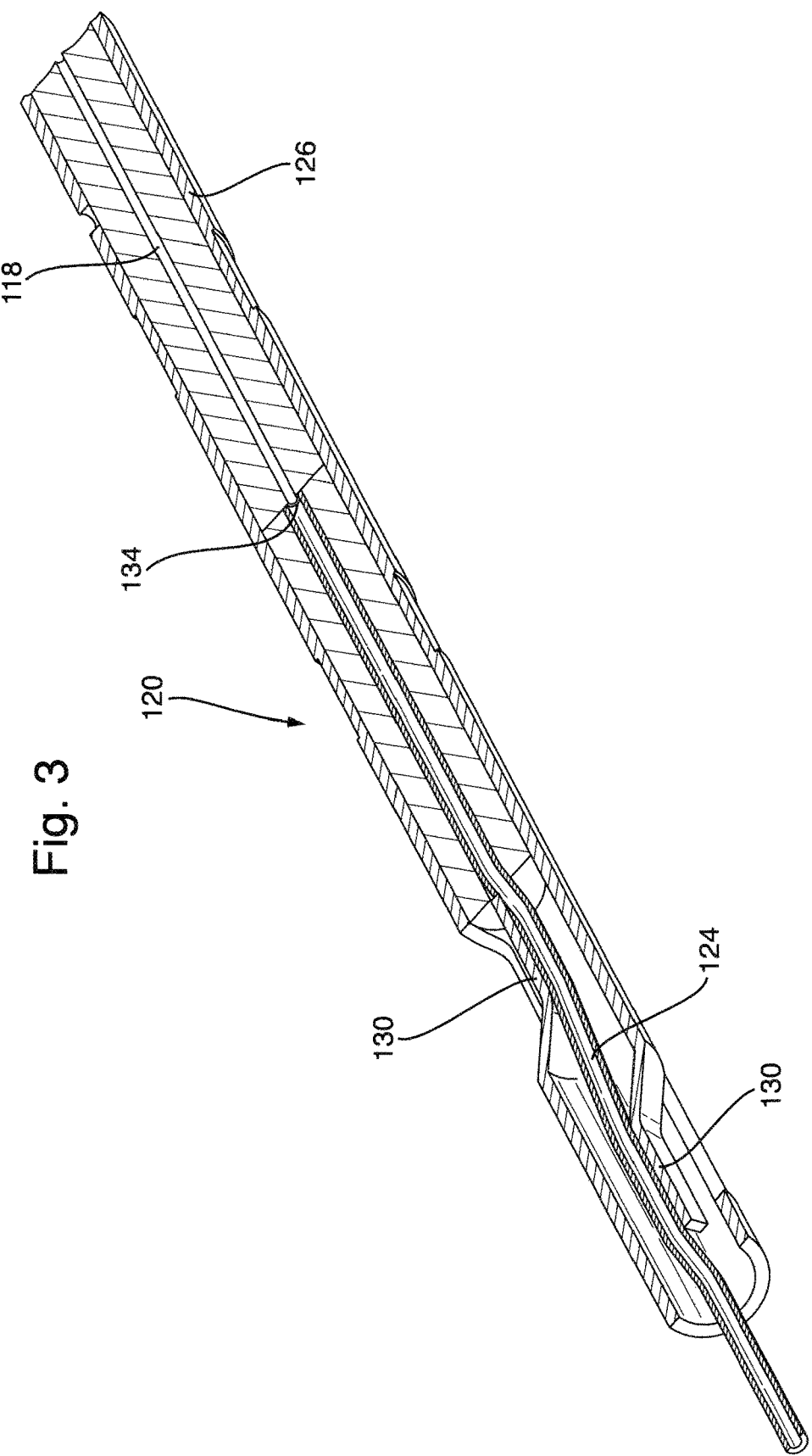

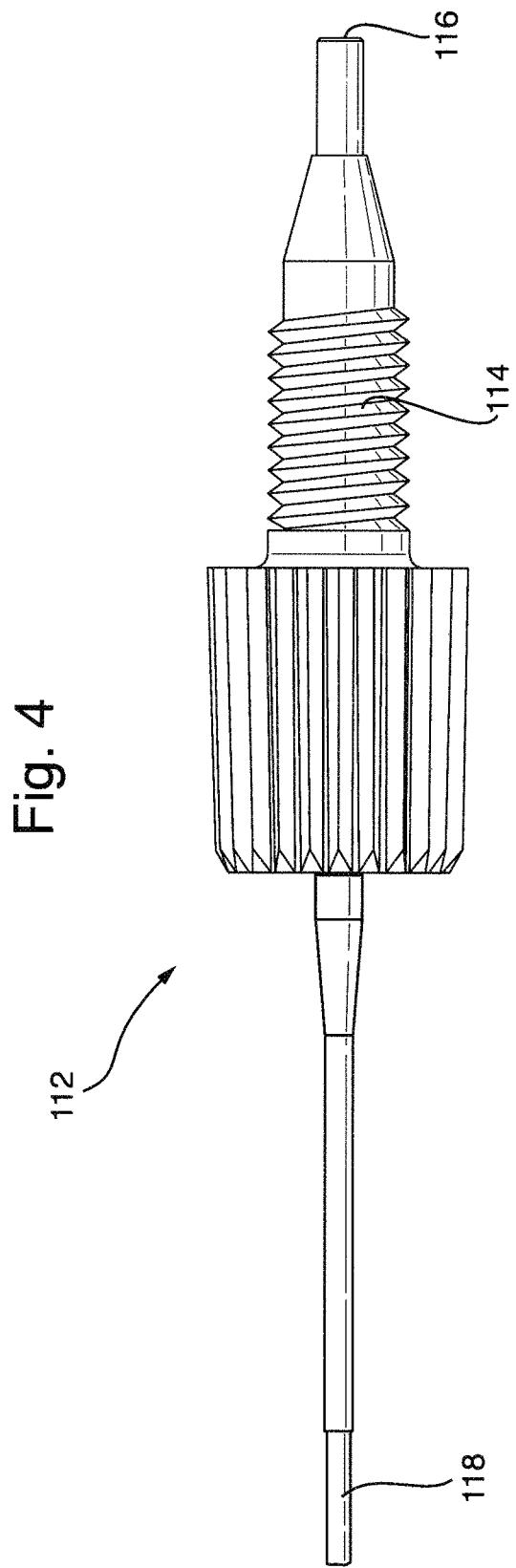

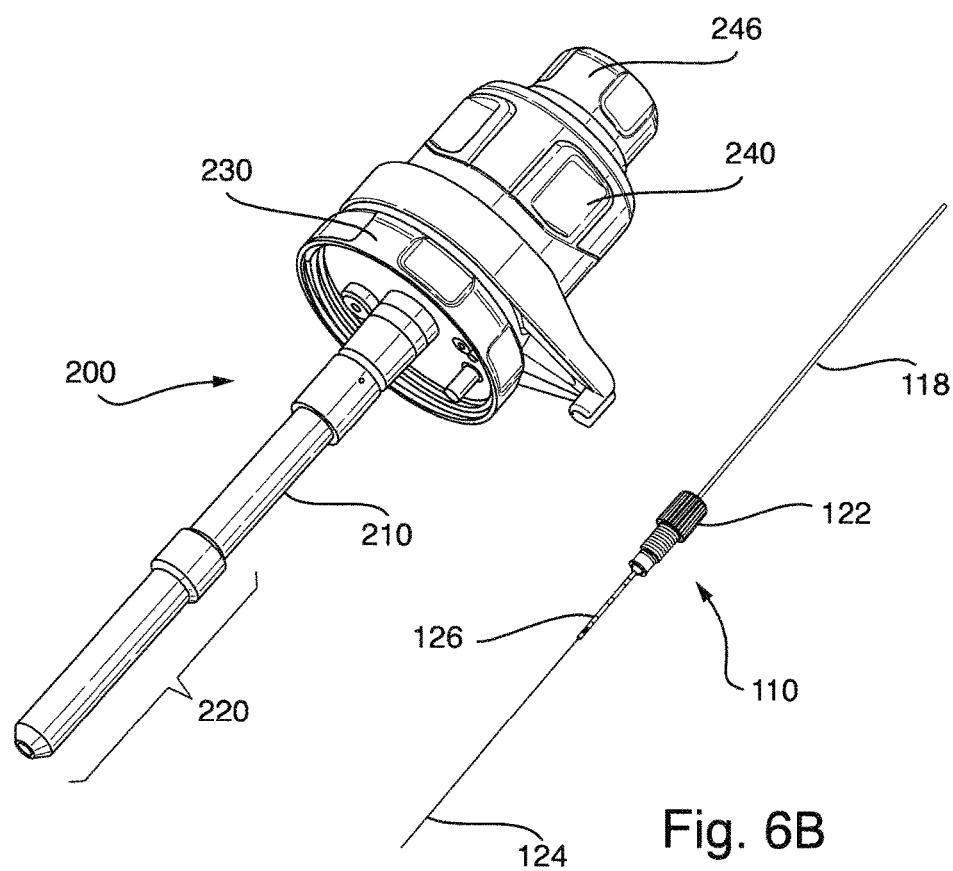

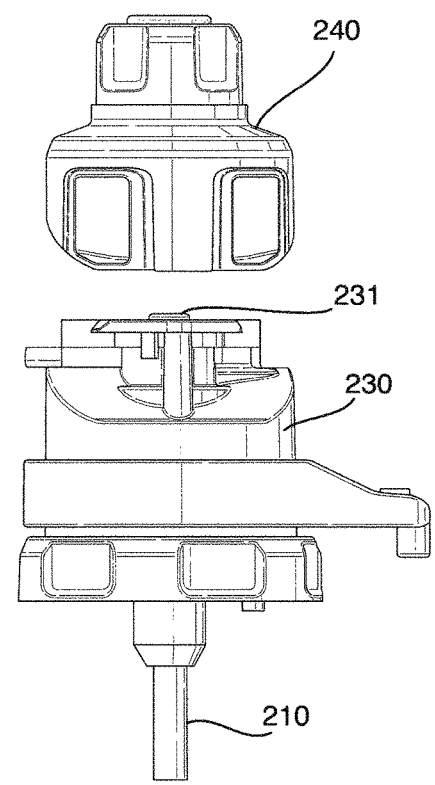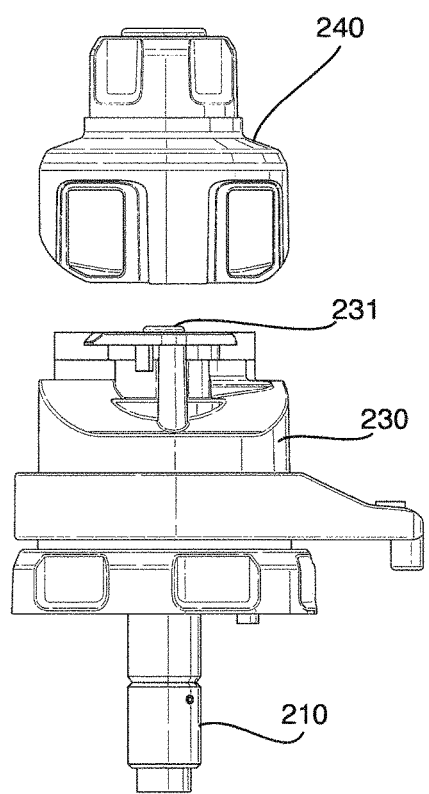

PROBE ADAPTOR ASSEMBLY

CROSS-REFERENCE TO RELATED APPLICATION

This application is a continuation of U.S. patent application Ser. No. 15/464,924, filed on 21 Mar. 2017 (now U.S. Pat. No. 9,947,522), which claims priority from and the benefit of United Kingdom patent application No. 1606124.4 filed on 11 Apr. 2016, and United Kingdom patent application No. 1606123.6 filed on 11 Apr. 2016. The entire contents of these applications are incorporated herein by reference.

FIELD OF THE INVENTION

This invention relates generally to mass and/or ion mobility spectrometers, and in particular to apparatus for coupling chromatography systems with ion sources and/or mass and/or ion mobility spectrometers.

BACKGROUND

Liquid chromatography systems are an important tool to the analytical chemist for the separation and analysis of samples of interest. Often, after separation in the liquid chromatograph, the components require further analysis to confirm the identity of these components. This may be performed using a mass and/or ion mobility spectrometer. However, connecting liquid chromatography systems to mass and/or ion mobility spectrometers can be a difficult and time consuming task.

Tubing may be used to deliver eluent to an ion source, wherein the eluent from the liquid chromatography system is sprayed into the ion source chamber through a capillary. This can result in an awkward connection that requires dexterity and skill to assemble. Moreover, there is a risk of electric shock at the connection for the user assembling the instrument connection, especially if there is a leak. The connecting assembly can also be expensive.

Furthermore, the fitting of the liquid chromatography tube connection into an ion source can take a long time, resulting in inactivity of the instrument. Poor instrument performance may also occur if parts are omitted or poorly assembled. This can result in dead volumes, which may lead to poor reproducibility or poor performance of the instrument.

The Applicant's earlier application GB-2520389 addresses these and other problems by providing a probe assembly for delivering eluent to a mass spectrometer, wherein a joint between an electrically insulated liquid line and a conductive capillary is provided downstream of an attachment device that attaches the probe to the spectrometer. This means that the eluent is less likely to leak out of the spectrometer when the probe is attached. A conductive member is provided in order to supply a voltage from the attachment device, downstream beyond the insulated liquid line and to the conductive capillary. This enables a voltage to be supplied relatively easily from the mass spectrometer to the conductive capillary via the attachment device, even though the electrically insulated liquid line is interposed between the attachment device and the conductive capillary. The structure of the probe therefore enables the electrical connection to be made between the spectrometer and the conductive capillary relatively quickly and easily.

Notwithstanding the benefits associated with the probe assembly described in GB-2520389, the Applicants believe that there remains scope for further improvements to mass and/or ion mobility systems in which an atmospheric pressure ionisation probe is coupled with mass and/or ion mobility spectrometer.

It is therefore desired to provide improved apparatus for mass and/or ion mobility spectrometry.

SUMMARY

According to a first aspect there is provided apparatus for connecting an ionisation probe assembly to a mass and/or ion mobility spectrometer, the apparatus comprising:

an attachment member for releasably attaching a probe assembly to the apparatus;

a cap for enclosing the attachment member;

wherein the apparatus is operable to deliver a voltage to a probe assembly only when the cap is arranged to enclose the attachment member; and wherein the cap is configurable to enclose the attachment member when a probe assembly is attached to the apparatus.

The cap may be configurable to enclose the attachment member when no probe assembly is attached to the apparatus (e.g. when the probe assembly is detached from the apparatus), e.g. so as to prevent a probe assembly or other object being brought into contact with the attachment member.

According to a second aspect there is provided apparatus for connecting an ionisation probe assembly to a mass and/or ion mobility spectrometer, the apparatus comprising:

an attachment member for releasably attaching a probe assembly to the apparatus;

a cap for enclosing the attachment member;

wherein the cap is configurable to enclose the attachment member when a probe assembly is attached to the apparatus; and wherein the cap is configurable to enclose the attachment member when no probe assembly is attached to the apparatus (e.g. when the probe assembly is detached from the apparatus) e.g. so as to prevent a probe assembly or other object being brought into contact with the attachment member.

According to various embodiments, apparatus is provided for connecting an ionisation probe assembly to a mass and/or ion mobility spectrometer. The apparatus may comprise an attachment member for releasably attaching the probe assembly to the apparatus and a cap for enclosing the attachment member, i.e. for preventing access to the attachment member. The apparatus may be operable to deliver a voltage to a probe assembly, e.g. via the attachment member, only when the cap is arranged to enclose the attachment member. The cap may be configurable to enclose the attachment member when a probe assembly is attached to the apparatus. The cap may be configurable to enclose the attachment member when no probe assembly is attached to the apparatus so as to prevent a probe assembly being brought into contact with the attachment member.

Accordingly, the risk of electrocution, the risk of a user coming into contact with potentially hazardous substances that may leak from the attachment member, the risk of leaks adversely affecting the instrument, and/or fire hazard risks are substantially reduced, both when a probe assembly is attached to the apparatus and/or when no probe assembly is attached to the apparatus.

It will be appreciated therefore that various embodiments described herein provide improved apparatus for mass and/or ion mobility spectrometry.

The apparatus may comprise an orifice.

The apparatus may be configured such that the probe assembly is insertable into the orifice The attachment member may be configurable to releasably secure the probe assembly within the orifice.

The attachment member may comprise or may be in electrical communication with an electrical contact for delivering the voltage from the apparatus to the probe assembly when the probe assembly is releasably attached to the apparatus.

The cap may comprise an aperture through which at least a portion of the probe assembly can pass.

The apparatus may comprise a device configured to close the aperture when the cap is arranged to enclose the attachment member and when no probe assembly is attached to the apparatus.

The device may be configured such that the aperture is openable only when the attachment member is not (is other than) enclosed by the cap.

The device may comprise one or more balls or other objects and one or more pockets for receiving the one or more balls or other objects.

The apparatus may comprise a probe tip configured to receive a capillary of the probe assembly.

The apparatus may comprise a device for controlling the position of the capillary relative to the probe tip.

The device may be configured such that the position remains substantially unaltered when a probe assembly is detached from and/or attached to the apparatus.

According to an aspect there is provided apparatus for connecting an ionisation probe assembly to a mass and/or ion mobility spectrometer, the apparatus comprising:

an attachment member for releasably attaching a probe assembly to the apparatus;

a probe tip configured to receive a capillary of the probe assembly; and a control device for controlling the position of the capillary relative to the probe tip.

The device may be configured such that the position remains substantially unaltered when a probe assembly is detached from and/or attached to the apparatus.

The probe tip may comprise a capillary configured to receive the capillary of the probe assembly.

The control device may be configured to control the position of the capillary relative to the probe tip capillary.

The apparatus may comprise a guiding member configured to guide the capillary into the probe tip capillary when the probe assembly is releasably attached to the apparatus.

The apparatus may comprise a cap for enclosing the attachment member.

The attachment member may be provided in a main body of the apparatus.

The cap may be releasably securable to the main body so as to enclose the attachment member.

The control device may be operable from an external surface of the cap.

The control device may comprise a first mechanism in the cap that is engagable with a second mechanism in the main body.

Operation of the control device may cause the position of the capillary relative to the probe tip to be altered via the first and second mechanisms.

The first and/or second mechanisms may be configured such that the position of the capillary relative to the probe tip remains substantially unaltered when the cap is secured to and/or released from the main body.

The apparatus may comprise a liquid drain.

The apparatus may comprise a device for collecting liquid incident upon at least a portion of the apparatus and for directing the liquid to the drain.

The drain may comprise one or more open-ended slots or indentations.

According to an aspect, there is provided apparatus for connecting an ionisation probe assembly to a mass and/or ion mobility spectrometer, the apparatus comprising:

an attachment member for releasably attaching a probe assembly to the apparatus;

a liquid drain; and a device for collecting liquid incident upon the apparatus and for directing the liquid to the liquid drain;

wherein the drain comprises one or more open-ended slots or indentations.

The apparatus as may comprise one or more fins, ridges, bumps or other protrusions configured to prevent blockage of the drain.

The position and/or orientation of the drain may be fixed.

According to an aspect there is provided an adaptor for connecting a ionisation probe assembly to a mass and/or ion mobility spectrometer, the adaptor comprising apparatus as described above.

According to an aspect there is provided a mass and/or ion mobility spectrometer comprising apparatus as described above.

According to an aspect there is provided a method of delivering eluent to a mass and/or ion mobility spectrometer comprising:

providing a probe assembly;

providing apparatus as described above;

releasably attaching the probe assembly to the apparatus using the attachment member; and supplying eluent to the probe assembly such that eluent is transmitted through the probe assembly into the spectrometer.

The probe assembly may comprise:

an inlet for receiving an eluent from a chromatography device;

an outlet for delivering the eluent to an ion source of a mass and/or ion mobility spectrometer; and an attachment device for attaching the outlet to the apparatus.

The outlet may comprise a (optionally electrically conductive) capillary and a (optionally electrically conductive) member surrounding at least part of the capillary.

The probe assembly may comprise a (optionally electrically insulating) liquid line for transporting eluent from the inlet to the capillary and a joint between the liquid line and the capillary, wherein the joint is downstream of the attachment device.

The member may be arranged to receive a voltage upon connection of the attachment device to the apparatus and the member may be arranged to be in electrical connection with the capillary.

The outlet of the probe assembly may be configured to be insertable into an orifice of the apparatus and the attachment device may be configured so as to releasably engage the orifice so as to releasably attach the probe to the apparatus.

The joint may be arranged in the probe so as to be downstream of the orifice (i.e. within the apparatus) when the attachment device is connected to the apparatus.

It will be appreciated that the term "downstream" used herein refers to the direction from the inlet end to the outlet end of the probe assembly and/or adaptor.

The attachment device may comprise a screw fitting, a clamp, a bayonet or any other suitable type of attachment.

The screw fitting may comprise threads that extend circumferentially around the liquid line for engaging an orifice in the apparatus into which the probe is inserted, in use. The screw fitting and threads may be on an outer surface of the attachment device. Alternatively, the releasable engagement may be provided by other attachment means, or any form of attachment means which does not require tools to fit.

The attachment device may comprise a first electrical contact for receiving the voltage from the apparatus when the attachment device is releasably connected thereto, wherein the electrical contact is connected to the member and the member is connected to the capillary for transmitting the voltage from the apparatus to the capillary. The electrical contact may be on an outer surface of the attachment device.

The electrical contact may be a ferrule.

The electrical contact (e.g. ferrule) may be an integral or non-integral part of the attachment device. The electrical contact may form part of the attachment device such that when the attachment device is releasably connected to the apparatus, the electrical contact is connected to the apparatus and the member for transmitting the voltage from the spectrometer to the capillary.

The member may surround the joint. The member may be able to transmit the voltage from the attachment device, downstream of the liquid line and to the capillary.

The member may be a (optionally electrically conductive) tube. The tube may extend from being in contact with the electrical contact on the attachment device to being in contact with the capillary.

The electrical connection from the member to the capillary may be performed by tabs in the member; and/or the electrical connection from the member to the capillary may be performed by an electrically conductive packing between the member and the capillary.

The member may be arranged to receive the voltage upon connection of the attachment device to the apparatus through an electrically conductive ferrule.

The capillary may be configured to spray eluent from its outlet.

The capillary may be configured so as to transmit the voltage to the eluent being sprayed therefrom for forming charged droplets of eluent.

The capillary may be an electrospray capillary or an atmospheric pressure chemical ionisation capillary.

The inlet for receiving the eluent may be spaced from the attachment device.

The probe may have an inlet attachment device disposed towards one end of the probe and an outlet attachment device disposed towards the other end of the probe.

The probe assembly may further comprise an inlet attachment device for attaching the inlet to a chromatography device.

The inlet of the probe may be configured to be insertable into an orifice of the chromatography device and the inlet attachment device may be configured so as to releasably engage the orifice so as to releasably attach the probe to the chromatography device.

The inlet attachment device may comprise a screw fitting, a clamp or a bayonet, or any other suitable type of attachment. The screw fitting may comprise threads that extend circumferentially about the liquid line for engaging an orifice in the chromatography device. The screw fitting and threads may be on an outer surface of the inlet attachment device. Alternatively, the releasable engagement may be provided by other attachment means, or any form of attachment means which does not require tools to fit.

According to another aspect there is provided a mass and/or ion mobility spectrometer adapted to be connectable with a probe adaptor as described herein.

According to another aspect there is provided a system comprising apparatus as described herein and the probe assembly described herein, wherein the outlet attachment device of the probe assembly and the apparatus are configured such that the outlet attachment device is releasably engagable with an orifice in the apparatus so as to connect the probe assembly to the apparatus with the probe assembly outlet inserted into the orifice.

The apparatus of the system may comprise a voltage supply and a second electrical contact located proximate to the orifice for supplying the voltage to the capillary of the probe assembly. The second electrical contact may be arranged and configured such that when the outlet attachment device of the probe assembly is engaged with the orifice, the second electrical contact engages with the first electrical contact on the outlet attachment device for supplying the voltage from the voltage supply to the capillary.

The apparatus may comprise a nebuliser tube and a gas supply for supplying gas through the nebuliser tube, and the probe outlet may be configured to be inserted through the orifice into the nebuliser tube.

The system may comprise a chromatography device, wherein the probe assembly has a probe inlet configured to be releasably attached to the chromatography device so as to receive eluent from the chromatography device.

The probe assembly may be arranged to receive eluent and deliver it through an orifice in a housing of a mass and/or ion mobility spectrometer.

The probe assembly may comprise:

a liquid line having a liquid inlet for receiving eluent;

a capillary joined to the liquid line for receiving the eluent and having a liquid outlet for delivering the eluent into the spectrometer;

an attachment member surrounding the liquid line, wherein the join between the liquid line and the capillary is located downstream of the attachment member, and wherein the attachment member is configured to releasably engage the apparatus when the capillary and part of the liquid line are inserted through said orifice;

a first electrical contact on the attachment member for engaging an electrical contact on the apparatus when the capillary and liquid line are inserted through the orifice and the attachment member is releasably engaged with the apparatus; and a conductive member extending downstream from the electrical contact, passed the join between the liquid line and the capillary, and into contact with the capillary for supplying a voltage from the first electrical contact to the capillary.

The join may be arranged in the probe so as to be downstream of the orifice when the attachment member is connected to the apparatus.

The attachment member may comprise a screw fitting, a clamp, a bayonet, or any other suitable type of fitting for releasably engaging the apparatus when the capillary and liquid line are inserted through the orifice.

The screw fitting may comprise threads that extend circumferentially around the liquid line for engaging an orifice in the apparatus into which the probe is inserted, in use. The screw fitting and threads may be on an outer surface of the attachment member. Alternatively, the releasable engagement may be provided by other releasable attachment means, or any form of attachment means which does not require tools to fit.

The first electrical contact may be on an outer surface of the attachment member. The first electrical contact may be a ferrule.

The electrical contact (e.g. ferrule) may be an integral or non-integral part of the attachment member. The electrical contact may form part of the attachment member such that when the attachment member releasably engages the apparatus, the electrical contact is connected to the apparatus and the member for transmitting the voltage from the apparatus to the capillary.

The member may be a (optionally electrically conductive) tube that extends from the first electrical contact on the attachment member to the capillary.

The electrical connection from the member to the electrically capillary may be performed by tabs in the member, and/or by an electrically conductive packing between the member and the capillary.

The capillary may be configured to spray eluent from its outlet.

The capillary may be configured so as to transmit the voltage to the eluent being sprayed therefrom for forming charged droplets of eluent.

The capillary may be an electrospray capillary or an atmospheric pressure chemical ionisation capillary.

The inlet for receiving the eluent may be spaced from the attachment member.

The attachment member may be disposed towards an outlet end of the probe assembly and the probe assembly may have another attachment member disposed towards an inlet end of the probe assembly for attaching the inlet to a chromatography device or other source of analyte solution.

The inlet of the probe may be configured to be insertable into an orifice of the chromatography device or other source of analyte solution and the inlet attachment member may be configured so as to releasably engage the orifice so as to releasably attach the probe assembly to the chromatography device or other source of analyte solution.

The inlet attachment member may comprise a screw fitting, a clamp, a bayonet or any other suitable type of fitting. The screw fitting may comprise threads that extend circumferentially about the liquid line for engaging an orifice in the chromatography device or other source of analyte solution. The screw fitting and threads may be on an outer surface of the inlet attachment member. Alternatively, the releasable engagement may be provided by other attachment means, or any form of attachment means which does not require tools to fit.

According to another aspect there is provided a system comprising apparatus and the probe assembly described herein, wherein the apparatus comprises a housing having an orifice therein for receiving the probe assembly therethrough, wherein the attachment member of the probe and the apparatus housing are configured such that the attachment member is releasably engagable with the orifice so as to connect the probe assembly to the apparatus with the capillary and part of the liquid line inserted through the orifice, wherein the apparatus comprises a voltage supply and a second electrical contact, and wherein the second electrical contact is arranged in the apparatus so as to engage the first electrical contact on the probe assembly when the probe assembly has been releasably engaged with the orifice.

The orifice may be located in an adaptor or in an ion source of a mass and/or ion mobility spectrometer such that the capillary of the probe assembly extends into the ion source when the probe assembly is releasably engaged with the apparatus.

The attachment member may have engaging elements that releasably engage with complementary engagement elements on the apparatus for enabling the releasable engagement of the probe assembly to the apparatus.

The engaging elements on the attachment member may be screw threads and the engaging elements on the apparatus may be complementary screw threads.

A seal may be provided on the attachment member and/or in the apparatus proximate the orifice for providing a liquid seal between the probe assembly and the apparatus when the probe assembly is releasably engaged with the apparatus.

The apparatus may comprise a nebuliser tube and a gas supply for supplying gas through the nebuliser tube, and the probe outlet may be configured to be inserted through the orifice into the nebuliser tube.

The system may comprise a chromatography device or other source of analyte solution or eluent, wherein the probe assembly may have a probe inlet configured to be attached to the chromatography device or other source so as to receive the solution or eluent.

The inlet of the probe may be configured to be insertable into an orifice of the chromatography device or other source of analyte solution and the probe assembly may have an inlet attachment member configured so as to releasably engage the orifice so as to releasably attach the probe assembly to the chromatography device or other source of analyte solution.

The inlet attachment member may have engaging elements that releasably engage with complementary engagement elements on the chromatography device or other source of analyte solution for enabling the releasable engagement of the probe assembly to the chromatography device or other source of analyte solution.

The engaging elements on the attachment member may be screw threads and the engaging elements on the chromatography device or other source of analyte solution may be complementary screw threads.

The inlet attachment member may comprise a screw fitting, a clamp, a bayonet or any other suitable type of fitting. The screw fitting may comprise threads that extend circumferentially about the liquid line for engaging an orifice in the chromatography device or other source of analyte solution. The screw fitting and threads may be on an outer surface of the inlet attachment member. Alternatively, the releasable engagement may be provided by other attachment means, or any form of attachment means which does not require tools to fit.

According to another aspect, there is provided a method of delivering eluent to a mass and/or ion mobility spectrometer comprising:

providing a system as described herein;

inserting the outlet end of the probe assembly into the orifice;

releasably engaging the attachment member of the probe assembly with the apparatus such that the first electrical contact of the probe assembly engages the second electrical contact of the apparatus; and supplying eluent into the liquid line such that the eluent is transmitted through the capillary and into the spectrometer.

The method may comprise ionising the eluent or analyte solution in the spectrometer.

The spectrometer may comprise one or more ion guides.

The spectrometer may comprise one or more ion mobility separation devices and/or one or more Field Asymmetric Ion Mobility Spectrometer devices.

The spectrometer may comprise one or more ion traps or one or more ion trapping regions.

The spectrometer may comprise a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser.

The spectrometer may comprise one or more energy analysers or electrostatic energy analysers.

The spectrometer may comprise one or more ion detectors.

The spectrometer may comprise one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter.

The spectrometer may comprise a device or ion gate for pulsing ions; and/or a device for converting a substantially continuous ion beam into a pulsed ion beam.

The spectrometer may comprise a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser.

The spectrometer may comprise a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprise a device arranged and adapted to supply an AC or RF voltage to the electrodes.

A chromatography detector may be provided, wherein the chromatography detector comprises either:

a destructive chromatography detector optionally selected from the group consisting of (i) a Flame Ionization Detector (FID); (ii) an aerosol-based detector or Nano Quantity Analyte Detector (NQAD); (iii) a Flame Photometric Detector (FPD); (iv) an Atomic-Emission Detector (AED); (v) a Nitrogen Phosphorus Detector (NPD); and (vi) an Evaporative Light Scattering Detector (ELSD); or a non-destructive chromatography detector optionally selected from the group consisting of: (i) a fixed or variable wavelength UV detector; (ii) a Thermal Conductivity Detector (TCD); (iii) a fluorescence detector; (iv) an Electron Capture Detector (ECD); (v) a conductivity monitor; (vi) a Photoionization Detector (PID); (vii) a Refractive Index Detector (RID); (viii) a radio flow detector; and (ix) a chiral detector.

The spectrometer may be operated in various modes of operation including a mass spectrometry ("MS") mode of operation; a tandem mass spectrometry ("MS/MS") mode of operation; a mode of operation in which parent or precursor ions are alternatively fragmented or reacted so as to produce fragment or product ions, and not fragmented or reacted or fragmented or reacted to a lesser degree; a Multiple Reaction Monitoring ("MRM") mode of operation; a Data Dependent Analysis ("DDA") mode of operation; a Data Independent Analysis ("DIA") mode of operation a Quantification mode of operation or an Ion Mobility Spectrometry ("IMS") mode of operation.

BRIEF DESCRIPTION OF THE DRAWINGS

Various embodiments will now be described, by way of example only, and with reference to the accompanying drawings in which:

FIG. 3 shows schematically a detailed view of the outlet end of the probe showing the capillary and surrounding member;

FIG. 4 shows schematically the inlet end of the probe assembly of FIG. 1 for being fitted into a liquid chromatography device;

FIGS. 6A and 6B show schematically a probe adaptor and a probe assembly in accordance with various embodiments;

FIG. 12A shows schematically an electrospray ionisation probe adaptor comprising in accordance an embodiment, and FIG. 12B shows schematically an atmospheric pressure ionisation probe adaptor comprising in accordance an embodiment;

DETAILED DESCRIPTION

Various embodiments will now be described. Various embodiments described herein are directed to apparatus for coupling a liquid chromatography system and/or an ionisation probe assembly, e.g. an atmospheric pressure ionisation probe, with an ion source and/or mass and/or ion mobility spectrometer, e.g. with the ionisation chamber of a mass and/or ion mobility spectrometer.

In general, the apparatus may be used for coupling any liquid based input with any spray ionisation process. For example, the liquid chromatography system may comprise any suitable liquid chromatography system such as a High Performance Liquid Chromatography ("HPLC") system, Ultra Performance Liquid Chromatography ("UPLC") system, convergence chromatography system, Supercritical Fluid Chromatography ("SFC"), and the like. Equally, the ion source may comprise any suitable ions source, such as an Electrospray Ionisation ("ESI") ion source, an Atmospheric Pressure Chemical Ionisation ("APCI") ion source, an impactor spray ion source, and the like.

The apparatus may comprise an adaptor, i.e. a device that is releasably attachable to the spectrometer, e.g. by inserting the adaptor into an orifice of the (ionisation chamber of the) spectrometer. Additionally or alternatively, some or all parts of the apparatus may form part of the spectrometer, i.e. may be integrated with the spectrometer.

The apparatus (i.e. the adaptor and/or spectrometer) may be configured such that the probe assembly is releasably attachable to the apparatus, e.g. by inserting the probe into an orifice of the apparatus.

Figure 1:
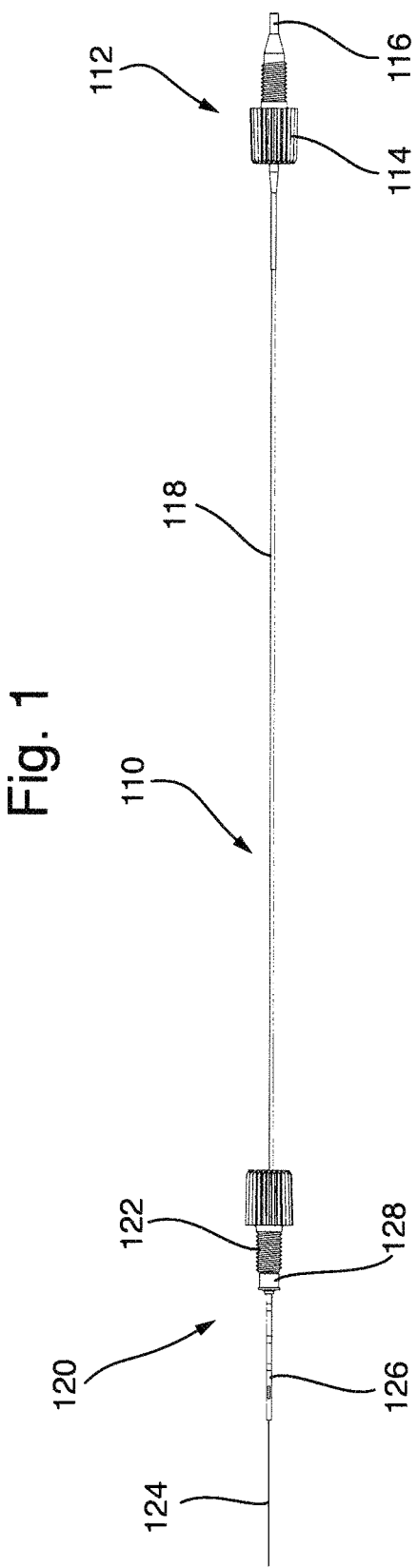
FIG. 1 shows schematically a probe assembly according to an embodiment.

FIG. 1 shows a probe assembly 110 according to an embodiment. The probe assembly 110 has an inlet end 112 having an inlet attachment fitting 114 that is configured for attaching the probe to a liquid chromatography device (not shown). A liquid inlet 116 is located at the inlet end 112 of the probe and is arranged to be insertable into a liquid chromatography output (not shown) such that the liquid inlet 116 receives eluent from the liquid chromatography instrument. An (optionally electrically insulating) liquid line 118, e.g. in the form of a silica capillary, runs from the liquid inlet 116 to an outlet end 120 of the probe. The inlet end 112 of the probe will be described in more detail in relation to FIG. 4.

Figure 2:
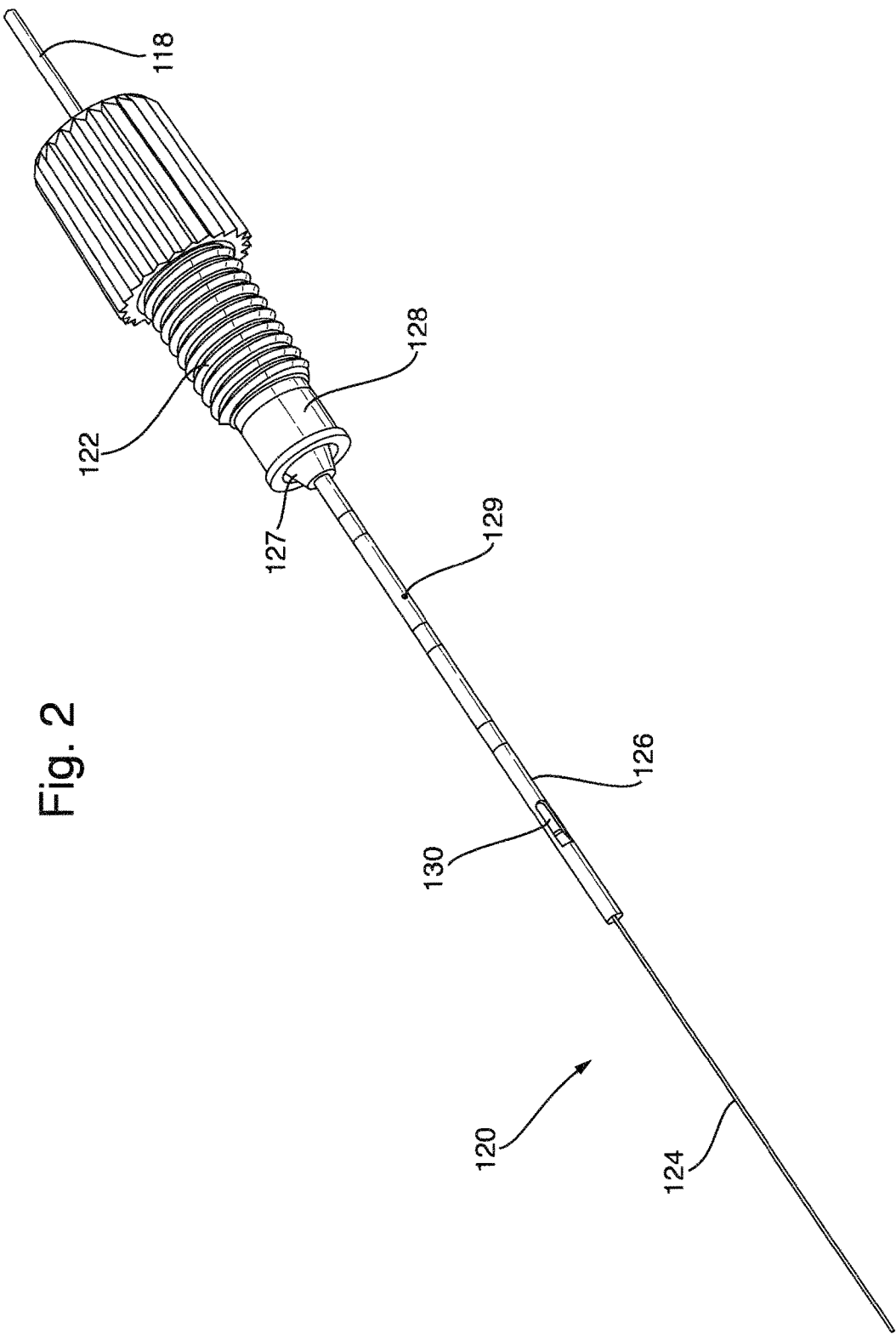
FIG. 2 shows schematically the outlet end of the probe assembly of FIG. 1 for being fitted into a mass and/or ion mobility spectrometer.

FIG. 2 shows the outlet end 120 of the probe assembly in more detail. In use, the outlet end 120 is inserted into the apparatus, e.g. into the adaptor or into the ion source of a mass and/or ion mobility spectrometer (not shown), and is releasably secured in the apparatus (adaptor or spectrometer) by the outlet attachment fitting 122. The attachment fitting may comprise any suitable type of fitting, e.g. may comprise a screw threaded portion on its external surface that engages with and is screwed into a complementary screw thread on the adaptor or spectrometer, a ratchet fitting, a screw torque fitting, one or more clips, a bayonet fitting, one or more screws, and the like, for securing the probe to the adaptor or spectrometer and/or for preventing the incorrect fitting of the outlet attachment device (e.g. by over tightening it).

The liquid line 118 runs from the liquid inlet 116 at the inlet end 112 to a (optionally electrically conductive) capillary 124 that forms a liquid outlet at the outlet end 120. The capillary 124 may be formed, for example, from steel. The capillary 124 makes a joint (not shown) with the liquid line 118 at a location downstream of the outlet attachment fitting 122. This is described in relation to FIG. 3. This arrangement may ensure that only electrically insulated tubing extends out of the adaptor or spectrometer from the attachment fitting 122, thereby reducing the risk of electrocution of the user.

The capillary 124 receives eluent from the liquid line 118 and delivers it into the spectrometer, when the outlet end 120 is attached to the spectrometer or adaptor (and the adaptor is attached to the spectrometer).

In some embodiments, it may be desired to supply a voltage to the (e.g. electrically conductive) capillary 124 whilst spraying eluent into the spectrometer. However, in other embodiments, a voltage may not be provided to the capillary 124. For example, the capillary 124 may be held at ground.

Where a voltage is supplied to the capillary 124, the voltage may be supplied by the adaptor or spectrometer to the outlet attachment fitting 122 and may then be conveyed from the outlet attachment fitting 122 to the capillary 124. However, as mentioned above, the fluid line 118, which may be electrically insulating, extends between the attachment fitting 122 and the capillary 124. As such, an (optionally electrically conductive) member 126, in the form of a tube, may be arranged to extend between an electrical connection on the attachment device 122 and the capillary 124, e.g. so as to transmit a voltage from the attachment device 122 to the capillary 124. The member 126 may cover the part of the liquid line 118 which passes downstream of the outlet attachment fitting 122, the joint (not visible) and part of the capillary 124. The end of the capillary 124 may be arranged to extend out from the (electrically conductive) tube 126. A conductive ferrule 127 may form the electrical connection on the outlet attachment fitting 122 that provides an electrical connection between the adaptor or spectrometer and the tube 126. An electrical connection (e.g. tabs 130) may also be arranged between the tube 126 and the capillary 124, e.g. to allow the voltage to pass to the capillary 124.

A liquid bleed hole 129 may be provided in the member 126 for allowing liquid to bleed into the adaptor or spectrometer source if the joint between the capillary 124 and the liquid line 118 fails. This may prevent liquid bleeding out of the adaptor or spectrometer, which may be a potential source of electrocution or cause hazards to the user and/or instrument.

FIG. 3 is a detailed cross-sectional illustration of a portion of the outlet end 120 of the probe assembly shown in FIGS. 1 and 2. The liquid line 118 may be joined to the capillary 124 at a joint 134 such that their bores are in fluid communication. The member 126 may extend from an electrical connection on the outlet attachment device 122 (not shown), over the joint 134 and into electrical connection with the capillary 124. As such, a voltage can be supplied from the attachment device 122 to the capillary 124 by the member 126, even though the fluid line 118 extends between the attachment device 122 and the capillary 124.

Metal tabs 130 may be cut into, or depressed in, the member 126, e.g. so that these tabs 130 of the member 126 contact the capillary 124. Where a voltage is supplied to the capillary 124, this contact may make (and be used to provide) an electrical connection between the two components.

Additionally or alternatively, the tabs 130 may be used in order to fix the capillary 124 in place relative to the member 126. At least two tabs 130 may be provided, wherein one tab 130 may be forced into contact with one side of the capillary 124 and another tab 130 may be forced into contact with the other side of the capillary 124. The tabs 130 may be arranged relatively close together at axially spaced apart locations. This arrangement serves to hold the capillary 124 in a substantially fixed radial position and ensures constant contact between the capillary 124 and the member 126.

FIG. 4 is a detailed view of the inlet end 112 of the probe assembly, i.e. the end to be fitted into the liquid chromatography system. As described in relation to FIG. 1, the inlet end 112 has an inlet attachment fitting 114 for attaching the probe to a liquid chromatography device (not shown). In use, the inlet end 112 of the probe may be inserted into the liquid chromatography device and releasably secured therein. The attachment device may include a fitting for engaging the liquid chromatography device so as to releasably secure the probe to the liquid chromatography device. Any suitable type of fitting may be provided, such as a screw threaded portion and/or ratchet mechanism for engaging a complementary profile on the liquid chromatography device, a screw torque fitting (e.g. for preventing the incorrect fitting of the outlet attachment device, e.g. by over tightening it), a bayonet fitting, one or more screws, one or more clips, and so on.

A liquid inlet 116 at the inlet end 112 is arranged to receive the eluent from the liquid chromatography instrument. A liquid line 118 runs from the inlet end 116 to the outlet end 120.

The probe may have a range of variants suited to different applications. For example, the probe may be provided with different bore sizes for the liquid outlet diameter, different variations of the length of the capillary, different capillary sizes (diameters) and different lengths of liquid line, and so on. The position of the joint, the lengths of the liquid line 118, member 126 and/or capillary 124, etc. can be varied and selected as desired.

Figure 5A:
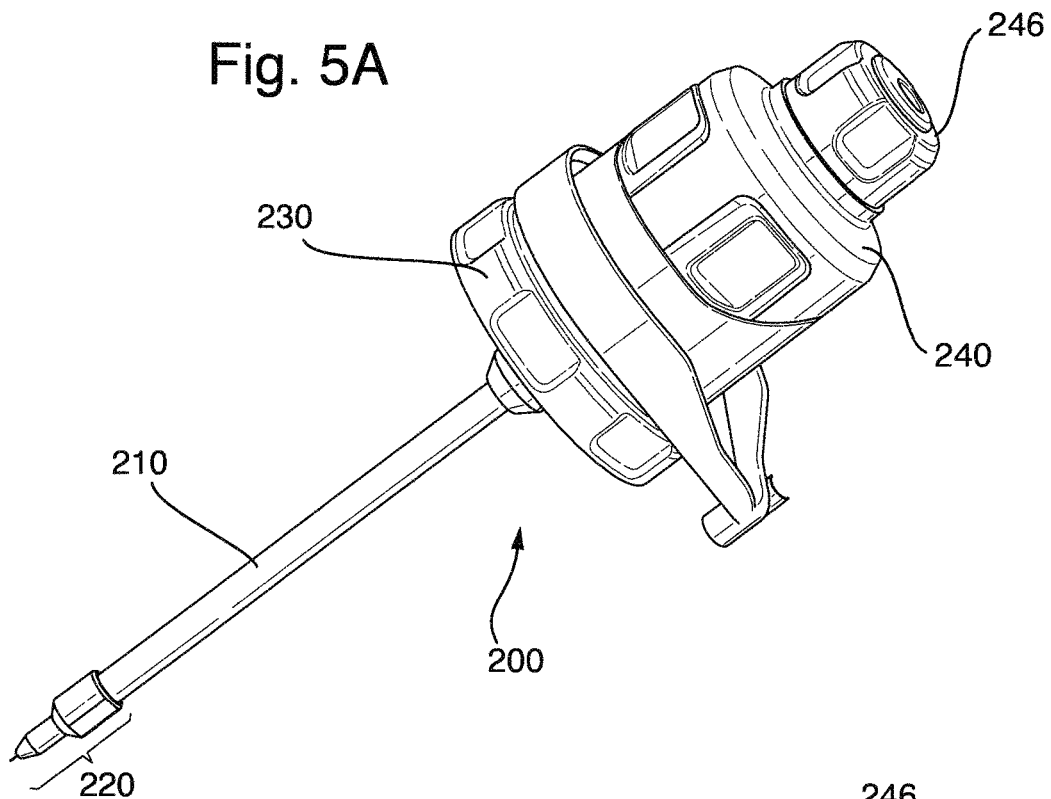
FIGS. 5A and 5B show schematically a probe adaptor in accordance with an embodiment.
Figure 5B:
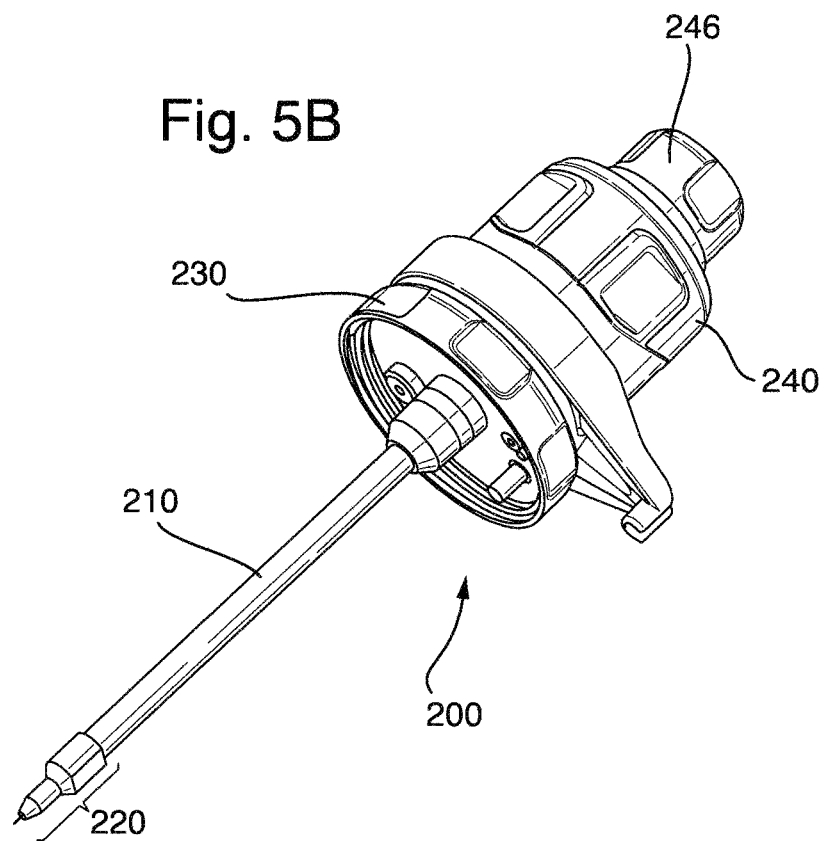
Figure 7:
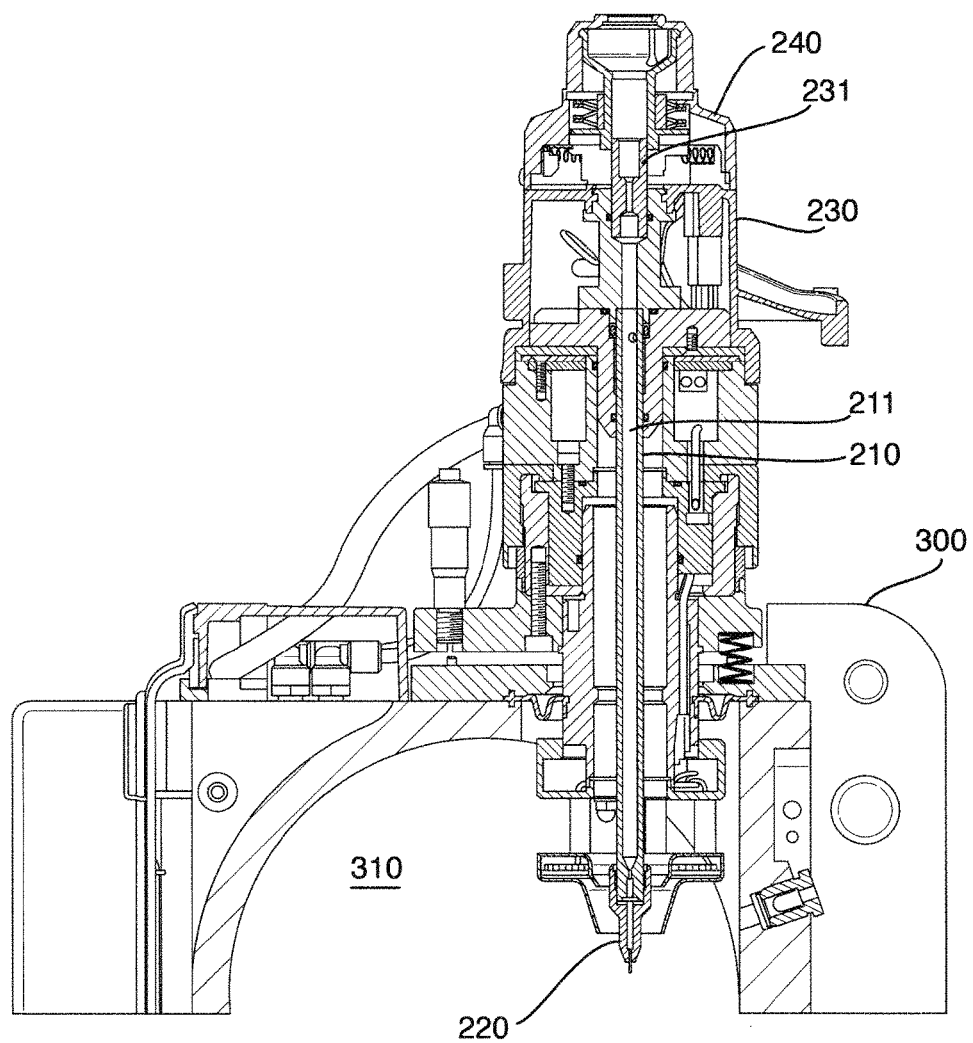
FIG. 7 shows the probe adaptor of FIGS. 5A and 5B installed in an ion source of a mass and/or ion mobility spectrometer.

FIGS. 5A and 5B show a probe adaptor 200 in accordance with an embodiment, and FIG. 7 shows the probe adaptor assembly 200 installed in an ion source 300 of a mass and/or ion mobility spectrometer in accordance with an embodiment. FIGS. 6A and 6B shows a probe adaptor 200 in accordance with another embodiment.

As shown in FIGS. 5A, 5B, and 6, the adaptor 200 generally comprises a tube member 210, a probe tip 220, a main adaptor body 230 and a cap 240 that releasably engages with the main adaptor body 230. The probe tip 220 is provided at the downstream end (i.e. the outlet end) of the tube member 210, and the main adaptor body 230 is provided at the upstream end (i.e. the inlet end) of the tube member 210. A part of the tube member 210, e.g. its upstream (inlet) end, may be provided inside the main adaptor body 230

The adaptor 200 is configured to be releasably secured to a mass and/or ion mobility spectrometer. In particular, as shown in FIG. 7, the adaptor 200 is configured to be insertable into an orifice of an ion source 300 of a mass and/or ion mobility spectrometer. When installed in the ion source 300, the tube portion 210 and the probe tip 220 are enclosed within the ion source 300, while the main adaptor body 230 and the cap 240 remain external to the ion source 300. The adaptor may be secured to the spectrometer by securing the main adaptor body 230 to the spectrometer.

As shown in FIG. 7, the adaptor 200 is configured such that when installed in the ion source 300, at least a portion of the probe tip 220 extends into an ionisation chamber 310 of the ion source 300. As will be described in more detail below, this allows eluent from the liquid chromatography system (not shown) to be sprayed into the ion source chamber 310 via the probe tip 220.

The adaptor 200 is further configured such that the outlet end 120 of a probe assembly can be inserted into an orifice in the adaptor 200, and can be releasably secured in the adaptor using the outlet attachment fitting 122. Accordingly, the adaptor 200 may comprise a complementary attachment fitting 231, e.g. a screw fitting comprising a screw threaded portion that is configured to engage with the screw threaded portion of the attachment fitting 122 of the outlet end 120 of the probe assembly, when the probe assembly screw threaded portion engages with and is screwed into the adaptor screw fitting. Any other suitable type of complementary fitting may be provided, e.g. as described above. The attachment fitting 231 is provided in the main adaptor body 230 of the adaptor.

The outlet attachment device 122 of the probe assembly 110 may comprise a housing and a cup 128, such as a PEEK cup, for providing a sealing face between the attachment device 122 and the adaptor 200 when the attachment device is inserted into the adaptor 200. The attachment device 122 may also comprise the ferrule 127 that may be used to make an electrical connection between the body of the adaptor (in which the probe is inserted) and the (conductive) member 126. The ferrule 127 and the peek cup 128 may be crimped to the line 118 such that they do not move or rotate relative to the line 118, capillary 124 or member 126. The attachment device housing may be rotatable about and/or slidable along the line 118 for use in attaching the attachment device 122 to the adaptor 200. The ferrule 127 and cup 128 may not rotate, but may sit in the housing. The attachment device housing may then be rotated so as to screw the attachment device 122 into the adaptor 200 so that the cup 128 forms a seal with the adaptor 200.

The adaptor 200 is configured such that when the outlet end 120 of the probe assembly is inserted into the adaptor 200 (via the orifice), the capillary 124, the member 126, the capillary joint 134 between the capillary 124 and the liquid line 118, and part of the liquid line 118 are substantially enclosed within the main adaptor body 230 and the tube member 210.

In some embodiments, a portion of the capillary 124 will extend beyond the probe tip 220, i.e. so that when the adaptor is installed in the ion source 200, the capillary 124 will extend beyond the probe tip 220 into the ionisation chamber 310. This may be the case, for example, where the ionisation source is an ESI ion source. In other embodiments, most or all of the capillary 124 may be enclosed within the tuber portion 210 and the probe tip 220, i.e. so that the capillary 124 will not extend beyond the probe tip 220 into the ionisation chamber 310. This may be the case, for example, where the ionisation source is an APCI ion source.

A portion of the attachment fitting 122 will also extend beyond the adaptor main body 230 (proud of the orifice), together with the liquid line 118 and inlet portion 112 of the probe.

In some embodiments, e.g. where the ionisation source is an ESI ion source, the tube member 210 of the adaptor 200 may comprise an internal nebuliser gas tube 211 that, when the probe assembly 110 is inserted into the adaptor 200 (via the orifice), surrounds the capillary 124, the member 126, the capillary joint 134 between the capillary 124 and the liquid line 118, and part of the liquid line 118.

In use, eluent received from the liquid chromatography device passes from the liquid inlet 116 of the probe assembly, through the liquid line 118, the capillary joint 134, through the capillary 124, to the liquid outlet 144, and into the ionisation chamber 310 of the spectrometer. A nebuliser gas flow is arranged to flow along the nebuliser gas tube 211 of the tube member 210 towards the outlet of the capillary 124. The gas flow will flow past the outlet of the capillary 124 into the ionisation chamber 310. This enhances or enables the spraying of the eluent from the capillary 124 into the ion source 300. A voltage on the capillary 124 at the liquid outlet transfers voltage from the capillary 124 to the eluent as it enters the ionisation chamber 310 causing ionisation to occur.

The high voltage may be applied to the tube member 210 internally within the adaptor or spectrometer and passed from the tube member 210 to the probe assembly 110 via the ferrule 128.

Figure 8:
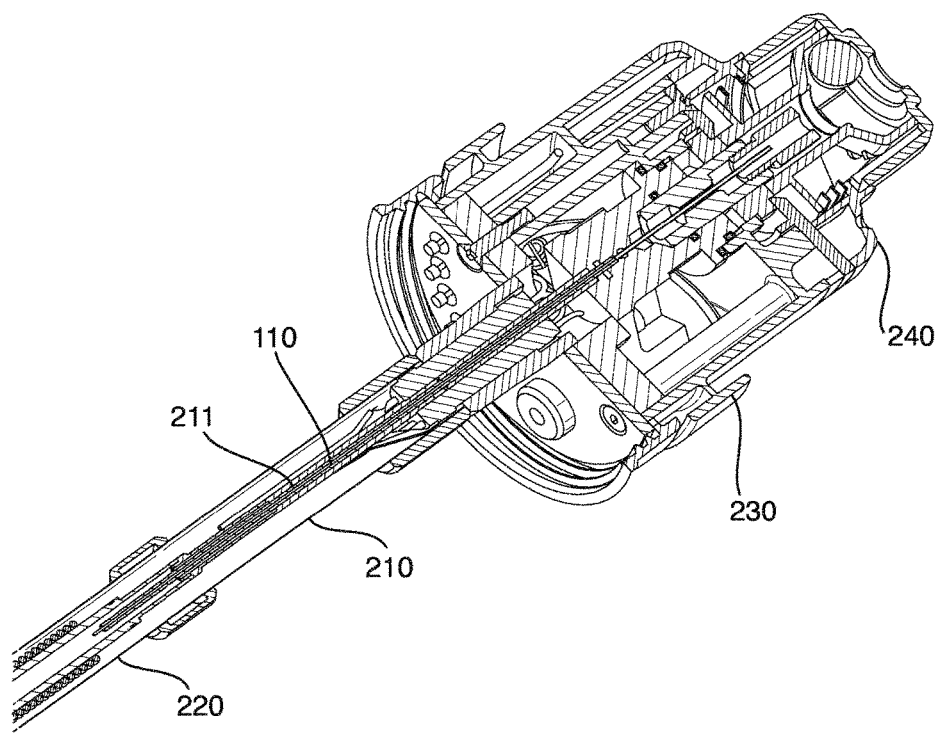
FIG. 8 shows schematically a probe adaptor and an installed probe assembly in accordance with an embodiment.

In other embodiments, e.g. where the ionisation source is an APCI ion source, as shown in FIG. 8, the tube member 210 of the adaptor 200 may comprise an internal nebuliser gas tube 211 that, when the probe assembly 110 is inserted into the adaptor 200 (via the orifice), surrounds the capillary 124, the member 126, the capillary joint 134 between the capillary 124 and the liquid line 118, and part of the liquid line 118.

In use, eluent received from the liquid chromatography device passes from the liquid inlet 116 of the probe assembly, through the liquid line 118, the capillary joint 134, through the capillary 124, to the liquid outlet 144, into the probe tip region 220, and then into the ionisation chamber 310 of the spectrometer. A nebuliser gas flow is arranged to flow along the nebuliser gas tube 211 of the tube member 210 towards the outlet of the capillary 124. The gas flow will flow past the outlet of the capillary 124 into the probe tip region 210. This enhances or enables the spraying of the eluent from the capillary 124 into the probe tip region 210. A heater may be provided in the probe tip region 210.

Figure 9:
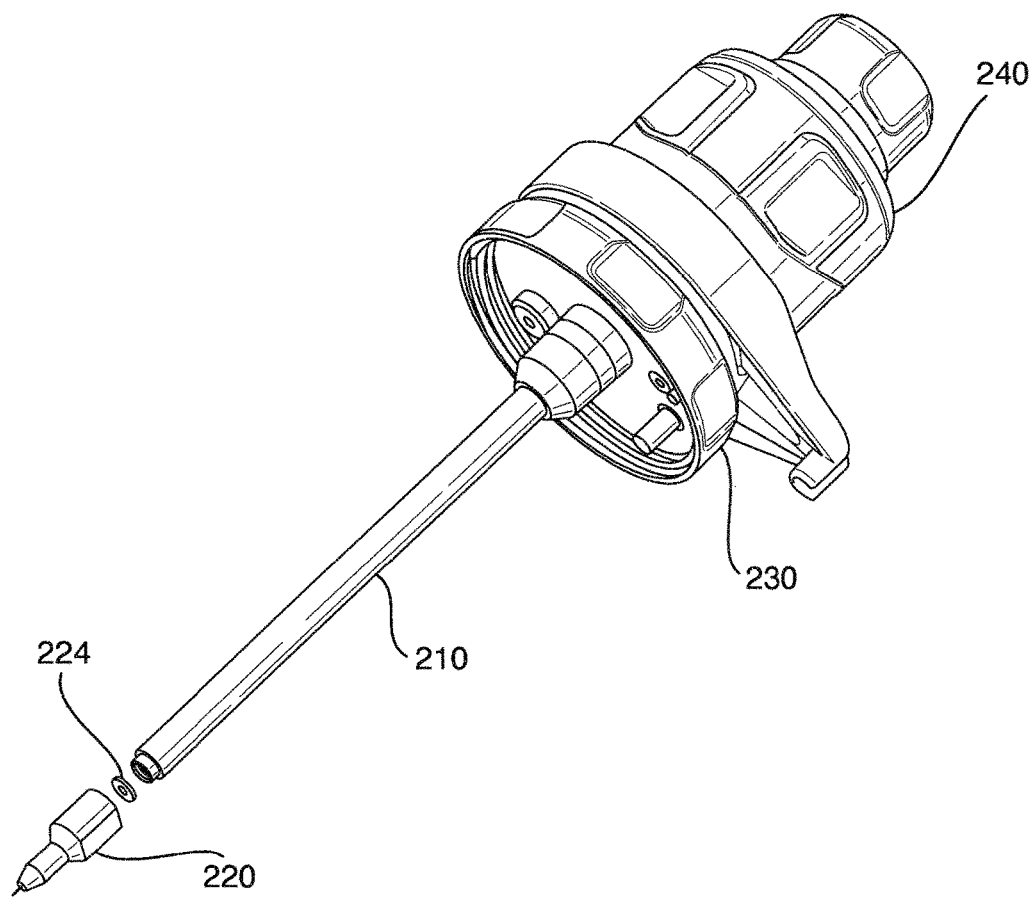
FIG. 9 shows schematically a probe adaptor in accordance with an embodiment.

FIG. 9 show a view of the probe tip 220 of the probe adaptor assembly 200. The probe tip 220 is releasably attachable to the outlet end of the tube member 210 of the adaptor 200. The probe tip 220 may be attached to the outlet end of the tube portion 210 by any suitable and desired means, such as by one or more screws, a screw fitting, a clamp, or a bayonet, optionally together with a washer or gasket 224.

The probe tip includes a nebuliser gas capillary 221 that extends though the main body of the probe tip 220. In some (ESI) embodiments, the downstream end of the nebuliser gas capillary 221 may protrude from the downstream end of the probe tip 220. In other (APCI) embodiments, the downstream end of the nebuliser gas capillary 221 is enclosed within the probe tip 220

When the probe tip 220 is attached to the tube member 210 of the adaptor 200, the upstream end of the nebuliser gas capillary 221 will extend into the downstream end of the nebuliser gas tube 211, and will be arranged to be in fluid communication with the downstream end of the nebuliser gas tube 211. The nebuliser gas capillary 221 may be substantially coaxially arranged with respect to the nebuliser gas tube 211.

When the probe assembly 110 is installed in the adaptor 200, the capillary 124 of the probe assembly is positioned within the nebuliser capillary 221, i.e. coaxially within the nebuliser capillary 221. A portion of the capillary 124 may extend beyond the nebuliser gas capillary 221, i.e. such that when the adaptor 200 is installed into the ion source 300, the downstream (outlet) end of the capillary 124 may extend into the ionisation chamber 310 (e.g. for ESI) or into the probe tip region 220 (e.g. for APCI).

In use, the nebuliser gas flow that flows along the nebuliser gas tube 211 is arranged to flow from the nebuliser gas tube 211 through the nebuliser gas capillary 221 and into the ionisation chamber 310 or into the probe tip region 220. As described above, the gas flow will flow past the outlet of the capillary 124 into the ionisation chamber 310 or into the probe tip region 220, to thereby enhance or enable the spraying of the eluent from the capillary 124 into the ion source 300 or into the probe tip region 220.

When installing the probe assembly 110 into the adaptor 200, the capillary 124 of the probe assembly must be passed through the nebuliser gas capillary 221.

Figure 10A:
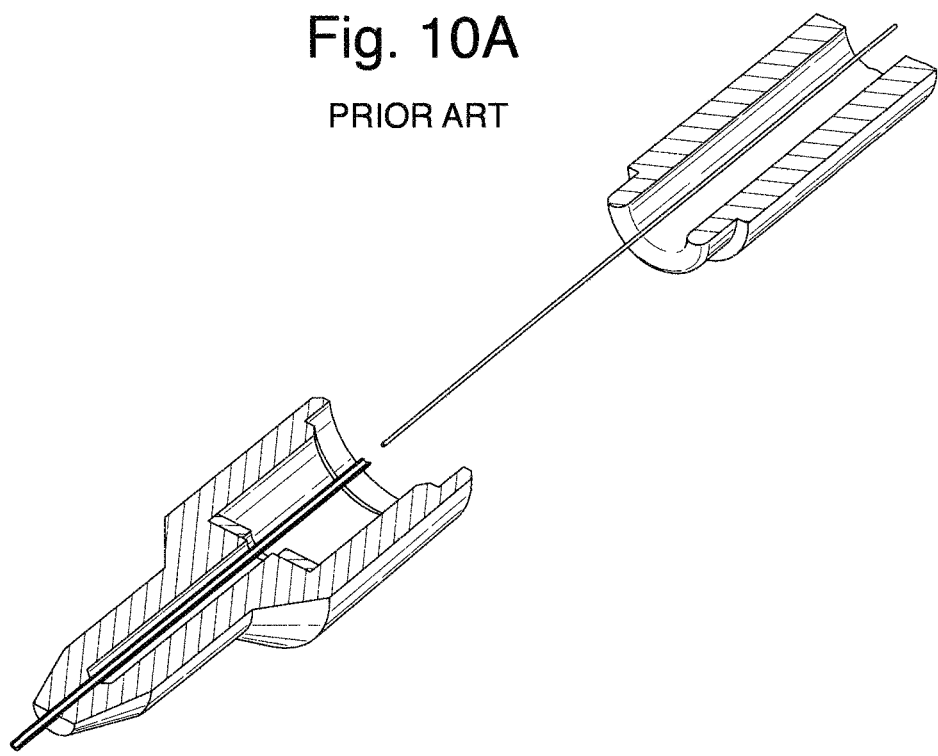
FIGS. 10A and 10B show schematically a conventional probe tip.
Figure 10B:
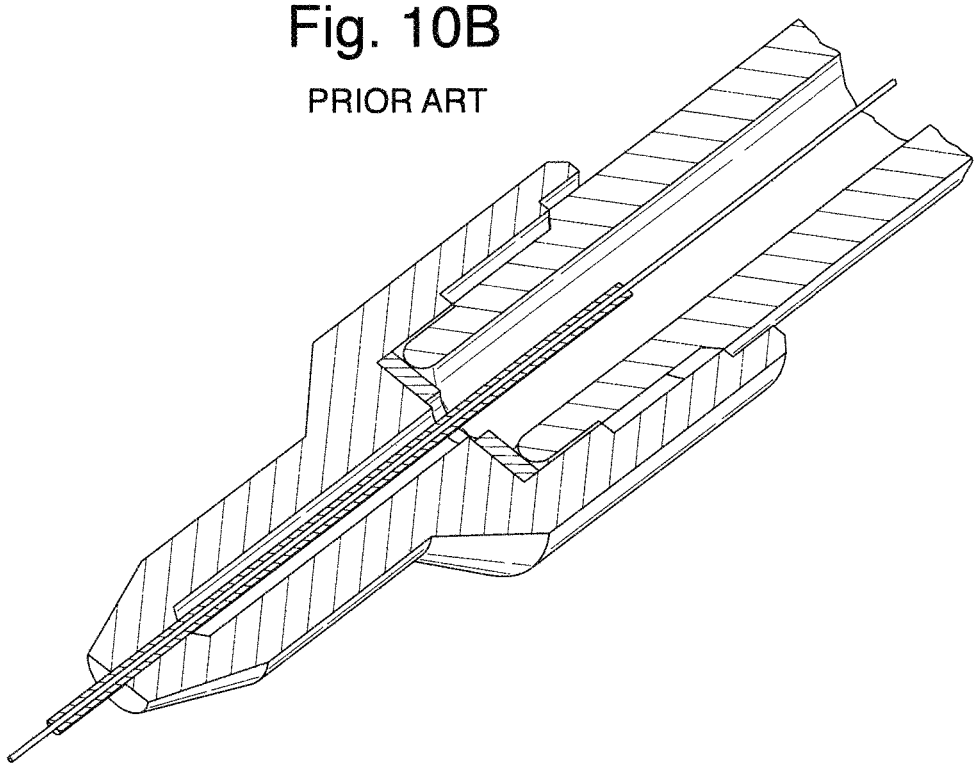

As illustrated by FIGS. 10A and 10B, this can be relatively difficult since the cross sectional area of the upstream entrance to the nebuliser gas capillary is relatively small, e.g. when compared with the total cross-sectional area of the nebuliser gas tube. This is particularly difficult when the probe assembly can only be handled from the opposite (inlet) end of the probe assembly.

Accordingly, the probe tip must typically be removed in order to install the probe assembly into the spectrometer. This allows the outlet end of the probe assembly (the outlet end of the capillary) to be handled and/or the probe tip itself to be handled so that the capillary can be threaded through the nebuliser gas capillary. Removing the probe tip typically requires tools, and can accordingly be an awkward and time-consuming task. It may also be necessary to open the ionisation chamber of the ion source, i.e. to the ambient atmosphere, in order to access and remove the probe tip, which can again add time and complexity to the task of installing the probe assembly.

Figure 11:
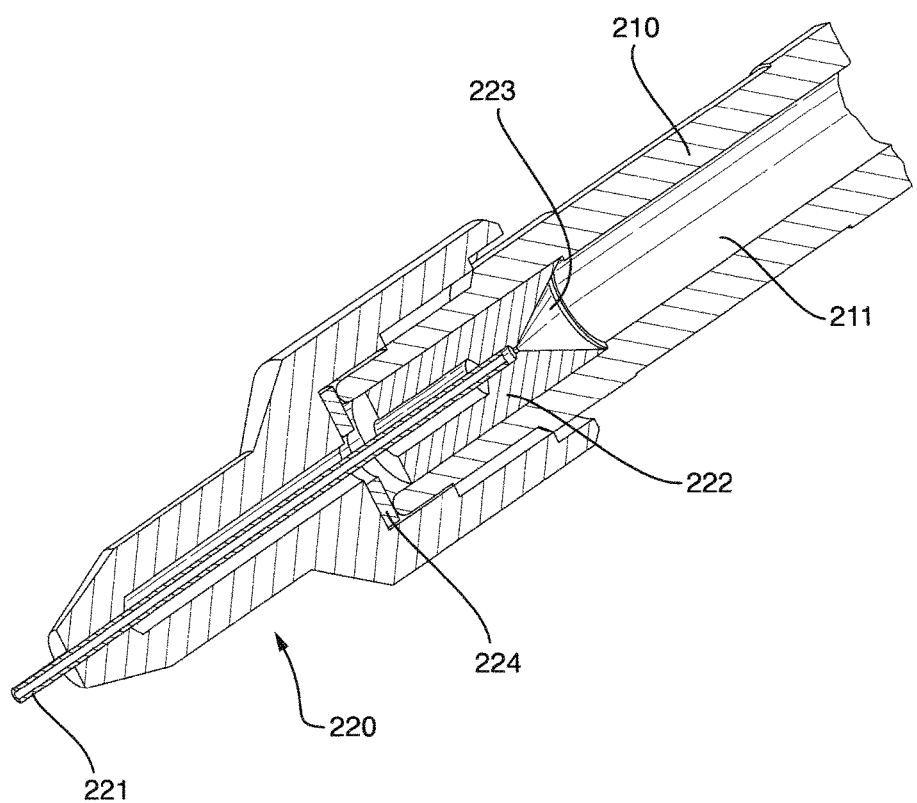
FIG. 11 shows schematically the probe tip of the probe adaptor of FIGS. 5A and 5B in more detail.

As shown in FIG. 11, according to various embodiments, the probe tip 220 comprises an internal guiding member 222 that is configured to allow the capillary 124 of the probe assembly to be located within the nebuliser gas capillary 221. The guiding member 222 may comprise, for example, a funnel 223 arranged at and in fluid communication with the upstream entrance to the nebuliser gas capillary 221. The funnel 223 may be arranged so as to be coaxially aligned with the nebuliser gas capillary 221, with the narrow end of the funnel 223 substantially adjacent to or in close proximity with the upstream entrance to the nebuliser gas capillary 221.

In this case, as the probe assembly 110 is inserted in to the adaptor 200, the capillary 124 of the probe assembly 110 will pass through the main body 230 of the adaptor, through the nebuliser gas tube 211 and towards the funnel 223 of the guiding member 222. When the outlet (downstream) end of the capillary 124 reaches the funnel 223 and as the probe assembly 110 is inserted deeper into the adaptor 200, the funnel 223 will act to guide the capillary 124 into and then through the nebuliser gas capillary 221.

Accordingly, the provision of a guiding member 222 in accordance with various embodiments removes the need for a user to accurately align the capillary 124 with the nebuliser gas capillary 221 when installing the probe assembly 110 in the adaptor or spectrometer. That is, the capillary 124 can be inserted into the nebuliser gas capillary 221 when handling the probe only from the opposite (inlet) end of the probe assembly. This in turn beneficially removes the need to remove the probe tip 220 when installing the probe assembly in the adaptor 200 or spectrometer. Equally, the adaptor need not be removed and/or the ion source need not be opened in order to install a probe assembly 110 in the adaptor or spectrometer.

Accordingly, the provision of a guiding member 222 according to various embodiments beneficially reduces the time required to install the probe assembly 110, and can facilitate tool-free installation of the probe assembly 110 in the adaptor 200 or spectrometer.

Nevertheless, as described above the probe tip 220 may be removed from the tube member 210 of the probe adaptor 200, e.g. for cleaning, maintenance, replacement, etc. Although this may require tools, the provision of the guiding member 222 means that the probe tip 220 need not be removed in order to install or remove the probe assembly 110.

FIGS. 12A and 12B show detailed views of the main body 230 and the cap 240 of the probe adaptor 200. The cap 240 is removably attachable to the main body 230 of the probe adaptor.

The adaptor 200 according to various embodiments may be configured such that any suitable type of atmospheric pressure ionisation ion source may be coupled to the mass and/or ion mobility spectrometer. In particular, as shown in FIG. 12A, the adaptor 200 may comprise an electrospray ionisation ("ESI") probe adaptor, and as shown in FIG. 12B, the adaptor may comprise an atmospheric pressure chemical ionisation ("APCI") probe adaptor. As will be appreciated, the provision of multiple types of adaptor means that the type of ionisation source that is coupled to the spectrometer can be changed in a relatively simple and convenient manner, i.e. by changing the adaptor.

As illustrated in FIGS. 12A and 12B, the caps 240 for the plural types of adaptor are substantially identical. Accordingly, the cap 240 may be universal for multiple types of adaptor.

Figure 13:
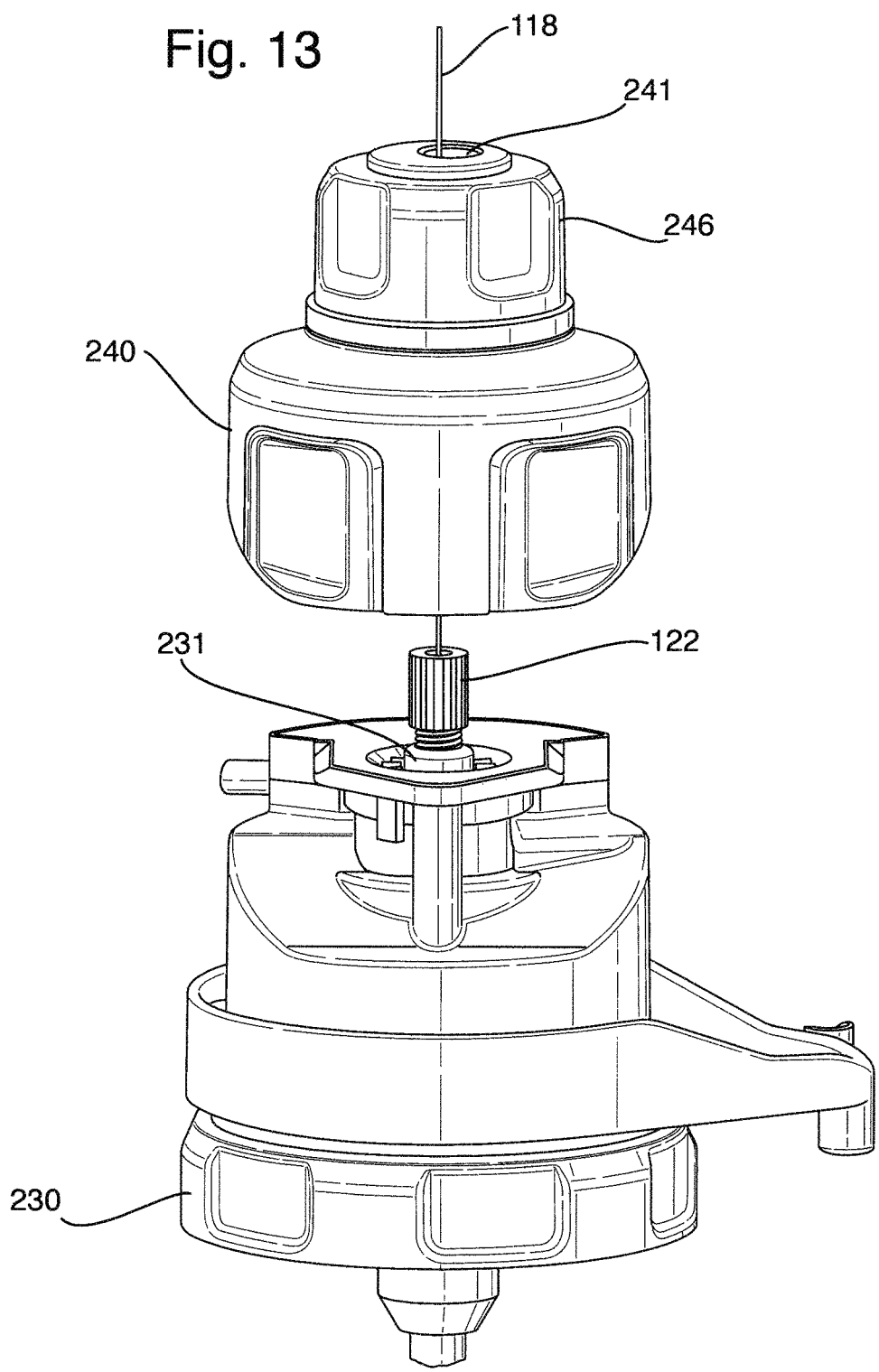
FIG. 13 shows schematically the cap and main adaptor body of the probe adaptor of FIGS. 5A and 5B in more detail.

As described above, the adaptor 200 is configured such that the outlet end 120 of the probe assembly can be inserted into the adaptor 200 via an orifice, and can be releasably secured in the adaptor, e.g. by screwing the outlet attachment fitting 122 into a screw threaded portion of an adaptor screw fitting 231. As shown in FIG. 13, a portion of the adaptor fitting 231 may extend beyond (may sit proud of) the main body 230 of the adaptor.

The adaptor 200 may be configured such that when the adaptor 200 supplies a voltage to the capillary 124 via the ferrule 127, the adaptor fitting 231 may receive a voltage. For example, the fitting 231 may form part of or may be in electrical contact with the tube member 210 and/or the nebuliser gas tube 211 to which the voltage is applied (and from which the voltage is passed to the probe assembly 110 via the ferrule 128). In this case, there is a risk of electrical shock if a user is able to access the fitting 231 when a voltage is being supplied to the capillary 124.

It would be possible to electrically isolate (at least) the portion of the fitting 231 that extends beyond the adaptor main body 230 to attempt to address this problem. In some embodiments, a voltage is not supplied to the capillary 124. However, liquid, e.g. due to a leak, within the fitting 231 or otherwise may form an electrical connection between one or more of the internal electrically conductive parts of the adaptor 200 (e.g. with ferrule 127 or the part of the adaptor 200 that provides the voltage to the ferrule 127 or otherwise) and the outside of the adaptor main body 230, e.g. in the vicinity of the fitting 231. The presence of liquid in the vicinity of the adaptor fitting 231 may be relatively common, for example due an eluent leak within the attachment device 122 or otherwise, e.g. due to a user incorrectly attaching the attachment device 122 of the probe assembly 110 to the adaptor 200.

Accordingly, there is in general a risk of electrical shock if a user is able to access the fitting 231 or its vicinity when a voltage is being supplied to the capillary 124.

Furthermore, contact with leaked eluent (which may comprise solvent) can also be hazardous to a user, even if the user wears gloves (e.g. if the solvent is able to pass through the gloves). In addition, the presence of solvent in the vicinity of the electrical components of the adaptor can be a fire hazard.

Accordingly, a cap 240 is provided, where the cap covers (encloses) the fitting 231 and its vicinity when the cap 240 is secured to the main body 230 of the adaptor 200. The cap 240 is configured such that a user cannot access the fitting 231 and its vicinity when the cap 240 is secured to the adaptor main body 230. In particular, the cap 240 is configured such that a user cannot introduce objects, such as a probe assembly 110, to the fitting 231 and its vicinity when the cap 240 is secured to the adaptor main body 230.

The adaptor 200 may further comprise a device configured to detect when the cap 240 is properly secured to the adaptor main body 230. The device may comprise, for example, a magnetic and/or voltage operated switch device. When it is detected that the cap 240 is secured to the main body 230, i.e. so as to prevent access to the fitting 231, then the voltage and/or an internal gas source or vacuum pump may be turned on (or the adaptor may be configured such that the voltage and/or an internal gas source or vacuum pump are able to be turned on). When it is detected that the cap 240 is not secured to the main body 230, i.e. such that the fitting 231 is accessible, then the voltage and/or an internal gas source or vacuum pump may be turned off (and/or the adaptor may be configured such that the voltage and/or an internal gas source or vacuum pump are unable to be turned on). This arrangement beneficially prevents a user coming into contact with the high voltage that may be applied to the capillary 124 via the adaptor 200 and/or leaked eluent, etc.

As shown in FIGS. 12A and 12B, the cap 240 is securable to the main adaptor body 230 so as to prevent access to the fitting 231 and its vicinity when a probe assembly 110 is not attached to (when the probe assembly 110 is detached from) the adaptor 200. The cap 240 should also be securable to the adaptor main body 230 (so as to prevent access to the fitting 231 and its vicinity) when a probe assembly 110 is attached to the adaptor 200. However, as described above, the inlet end 112 of the probe assembly 110 is, in use, attached to a (separate) chromatography device.

Accordingly, as shown in FIG. 13, the cap 240 includes an aperture 241 through which at least a portion of the probe assembly 110 can pass. The aperture 241 may be shaped and/or sized such that the inlet end attachment fitting 114 of the probe assembly 110 can pass through the aperture 241, e.g. such that the inlet end attachment fitting 114 of the probe assembly 110 can only just pass through the aperture 241, i.e. so as to prevent larger objects and/or other incompatible types of probe from passing though the aperture 241.

The aperture 241 is arranged such that when the probe assembly 110 is installed in the adaptor 200, the liquid line 118 can pass through the aperture 241, e.g. when the cap 240 is secured to the main adaptor body 230. The aperture 241 may be arranged such that when the cap 240 is secured to the adaptor main body 230, then the aperture is substantially aligned with the orifice/fitting 231 in the main body 230. The aperture 241 and the orifice/fitting 231 may or may not be coaxially aligned. For example, at least a portion of the aperture 241 may intersect with a central longitudinal axis of the orifice, where the portion of the aperture 241 that intersects with the axis may be the centre of the aperture 241, or some other non-central part of the aperture 241.

FIG. 13 shows a detailed view of the adaptor main body 230 and the cap when a probe assembly 110 is inserted into the adaptor 200. As shown in FIG. 13, when the probe assembly 110 is installed in the adaptor 200, the attachment device 122 of the probe assembly 110 is attached to (e.g. screwed into) the fitting 231 of the adaptor main body 230. In this configuration, (most of) the capillary 124, the member 126, the capillary joint 134 between the capillary 124 and the liquid line 118, and part of the liquid line 118, which are not visible in FIG. 13, will be enclosed within the adaptor main body 230 and the adaptor tube member 210. A portion of the attachment 122 extends beyond the fitting 231 externally to the adaptor main body 230. The portion of the line 118 upstream of the attachment device 122 extends from the attachment device 122, through the aperture 241 in the cap 240 and onwardly to the chromatography device (not shown).

The cap 240 is configured such that when the probe assembly 110 is installed in the adaptor 200, and the cap 240 is secured in place, access to the fitting 231 and its vicinity is restricted by the cap 240. Accordingly, the risk of electrical shock, contact with solvent, etc., is reduced.

However, the provision of the aperture 241 in the cap 240 may allow access to the fitting 231 or its vicinity when the probe assembly 110 is detached from the adaptor 200, and when the capillary voltage is being supplied to the capillary 124, i.e. when the cap 240 is secured to the main adaptor body 230.

Accordingly, the cap 240 is provided with a device for closing the aperture 241 and/or otherwise preventing access to the fitting 231 or its vicinity via the aperture 241 when the cap 240 is secured to the adaptor main body 230 and when a probe assembly 110 is not attached to the adaptor 200 (when the probe assembly 110 is detached from the adaptor 200).

Figure 14A:
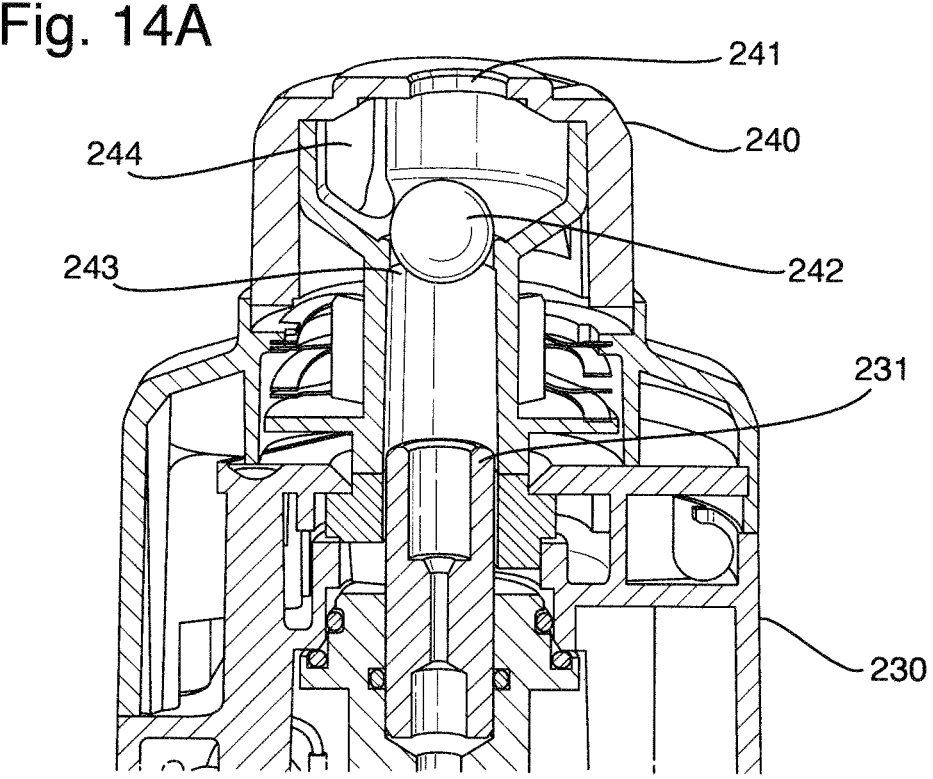
FIGS. 14A and 14B show schematically a cut away view of the cap and main adaptor body of the probe adaptor of FIGS. 5A and 5B when the cap aperture is closed.
Figure 14B:
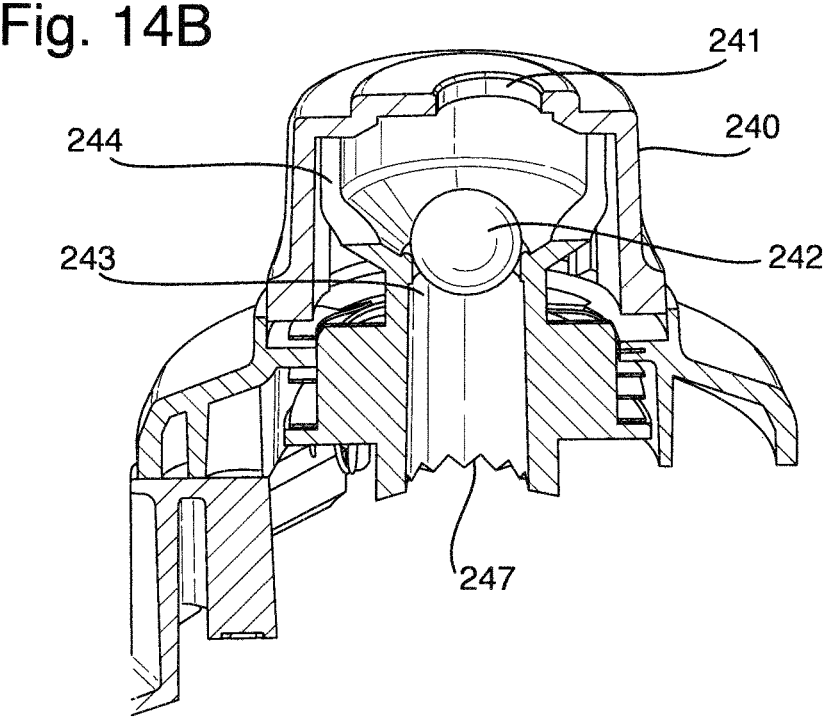

The device may take any suitable form, but as shown in FIGS. 14A and 14B the device may beneficially take the form of one or more balls, e.g. a ball bearing 242, provided internally within the cap 240. However, the device need not be in the form of a ball, and may comprise some other object provided internally within the cap. The cap 240 may be configured such that the ball 242 or other object may freely move within an internal hollow portion of the cap 240, but such that the ball or other object is contained within the cap 240, i.e. cannot be removed from the hollow portion of the cap 240 in normal operation (without e.g. dismantling the cap 240). Accordingly, the ball bearing 242 or other object and/or aperture 241 has an appropriate size and/or shape such that the ball 242 or other object cannot pass though the aperture 241, e.g. the diameter of the ball 242 or other object is greater than the diameter of the aperture 241. However, the cap 240 may be configured such that the ball 242 or other object cannot fully seal the aperture 241.

As shown in FIGS. 14A and 14B, the hollow portion of the cap 240 may comprise a first internal pocket 243 for receiving the ball 242 or other object. The first pocket 243 is configured such that the ball bearing 242 or other object cannot leave the internal hollow portion of the cap 240 via the first pocket 242, e.g. a (minimum) internal diameter of the pocket 243 is less than the diameter of the ball 242 or other object. The cap 240 is configured such that when the cap 240 is in or is close to an upright position (i.e. when a central longitudinal axis of the cap 240 is substantially vertical, e.g. when the cap 240 is secured to the adaptor main body 230) (and when a probe assembly 110 is not installed in the adaptor 200), then the ball bearing 242 or other object will fall (under the influence of gravity) into the first pocket 243. For example, the cap 240 may comprise a funnel portion arranged such that when the cap 240 is in or is close to an upright (vertical) position the ball 242 or other object will fall within the funnel portion under the influence of gravity into the first pocket 243.

The cap 240 is configured such that when the ball bearing 242 or other object is positioned within the first pocket 243 (and when the cap 240 is secured to the adaptor main body 230), then the ball bearing 242 or other object prevents access to the screw fitting 231 or its vicinity via the aperture 241.

As will be appreciated, this arrangement prevents the probe 110 assembly from coming into contact with the fitting 231 or its vicinity, e.g. if an inexperienced user attempts to insert the probe assembly 110 into the adaptor 200 when the cap 240 is closed (and therefore when a voltage is potentially being applied to the capillary 124). This also prevents other objects (e.g. fingers, tools, etc.) from coming into contact with the fitting 231 or its vicinity when the cap 240 is closed. The risk of electrical shock or contact with solvent to the user is therefore substantially reduced.

Figure 15:
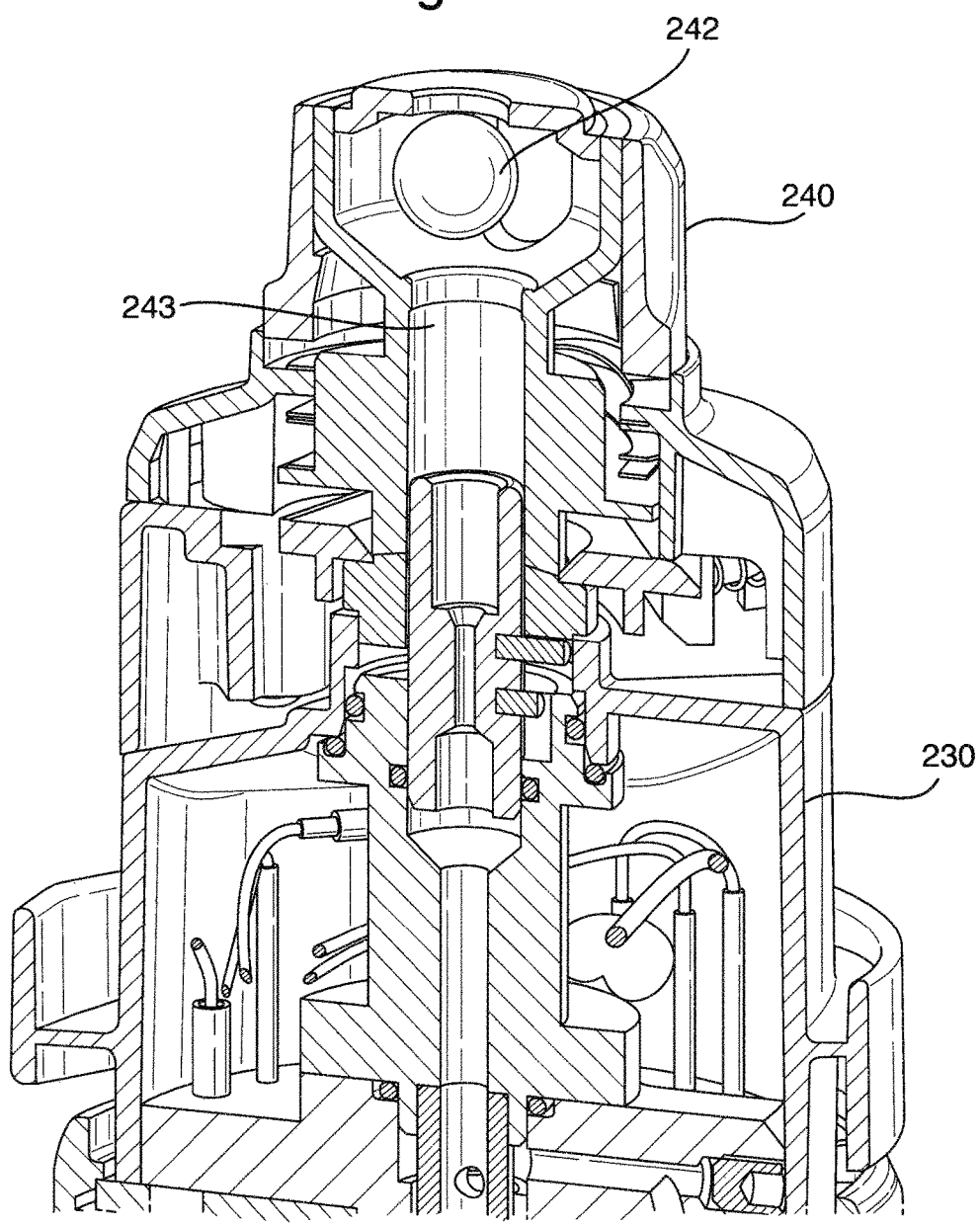
FIG. 15 shows schematically a cut away view of the cap and main adaptor body of the probe adaptor of FIGS. 5A and 5B.

The cap 240 may be configured such that the ball 242 or other object cannot fully seal the aperture beneath the first internal pocket 243. As shown in FIG. 15, when the ionisation region 310 of the ion source and/or tube portion 210 is pressurised, the ball 242 or other object may be configured to be ejected from the first internal pocket 243. In this case, an audible hiss from gas escaping via the adaptor 200 may alert the user to the fact that a probe assembly is not installed.

When installing the probe assembly 110 into the adaptor 200, the probe assembly 110 is passed through the aperture 241 in the cap 240. However, the ball 242 or other object may interfere with this operation. Accordingly, one or more second pockets 244 are provided in the internal hollow portion of the cap 240 for receiving the ball 242 or other object.

Figure 16A:
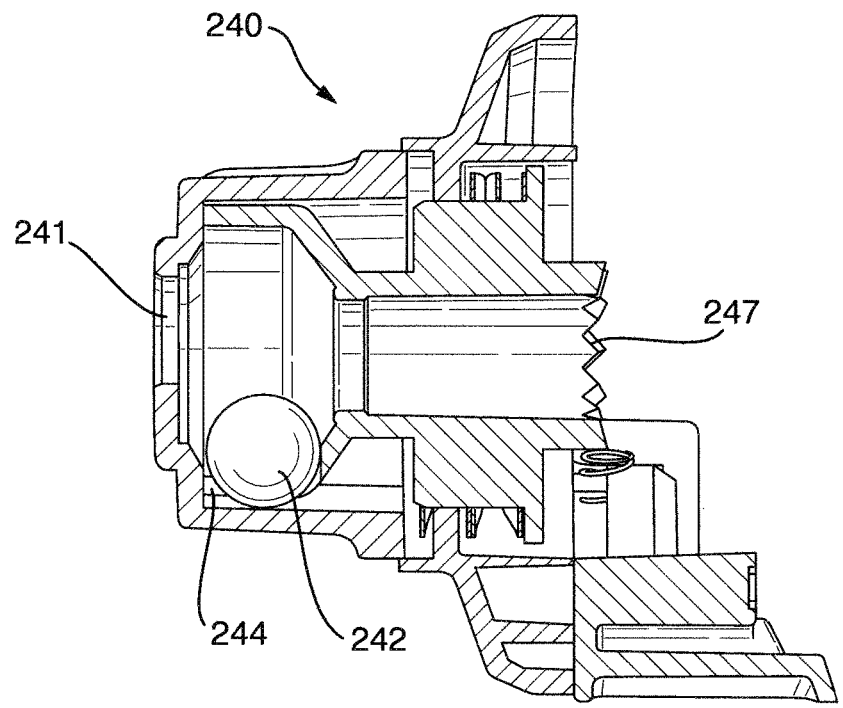
FIGS. 16A and 16B show schematically a cut away view of the cap of the probe adaptor of FIGS. 5A and 5B when the cap aperture is open.
Figure 16B:
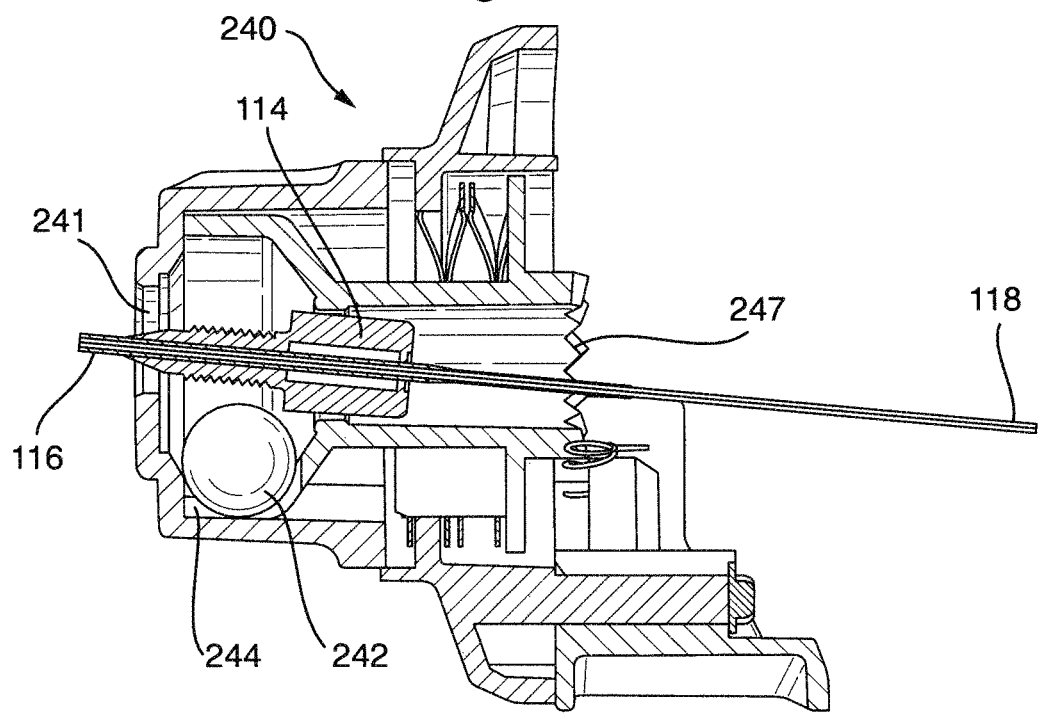

As shown in FIGS. 16A and 16B, the one or more second pockets 244 may be arranged such that when the cap 240 is not in or is not close to the upright (vertical) position (e.g. when the cap 240 is in or is close to a horizontal position), then the ball bearing 242 or other object will fall (under the influence of gravity) into one or the one or more second pockets 244. For example, tilting the cap 240 sufficiently far away from the upright position may cause the ball 242 or other object to move into one of the one of more second pockets 244.

The adaptor 200 is generally arranged such that it is necessary to remove the cap 240 from the main adaptor body 230 in order to rotate the cap 240 sufficiently far away from the upright position to cause the ball 242 or other object to move into one of the one or more second pockets 244. Accordingly, the aperture 241 is openable only when the adaptor 200 is not supplying the voltage to the capillary 124.

The cap 240 should be configured such that when the cap 240 is rotated by 90 degrees relative to the upright (vertical) position (about a rotation axis orthogonal to the central longitudinal axis of the cap 240) then the ball bearing 242 or other object will fall into one of the one or more second pockets, but the cap 240 may also be configured such that the ball bearing 242 or other object will fall into one of the one or more second pockets when the cap 240 is rotated by less than 90 degrees relative to the upright (vertical position). The angle or angles relative to the upright (vertical) position at which the cap 240 must be held in order for the ball bearing or other object to fall into one of the one or more second pockets 244 may be selected as desired.

As shown in FIG. 16B, the cap 240 is configured such that when the ball bearing 242 or other object is positioned within one of the one or more second pockets 244 then the aperture 241 is opened, i.e. so that the probe assembly 110 can be passed through the aperture 241, e.g. without the ball 242 or other object interfering with this operation.

The one or more second pockets may comprise a single pocket, e.g., that extends in a loop around the aperture 241 (as shown in FIGS. 16A and 16B), or may alternatively comprise any suitable plural number of discrete pockets.

Figure 17:
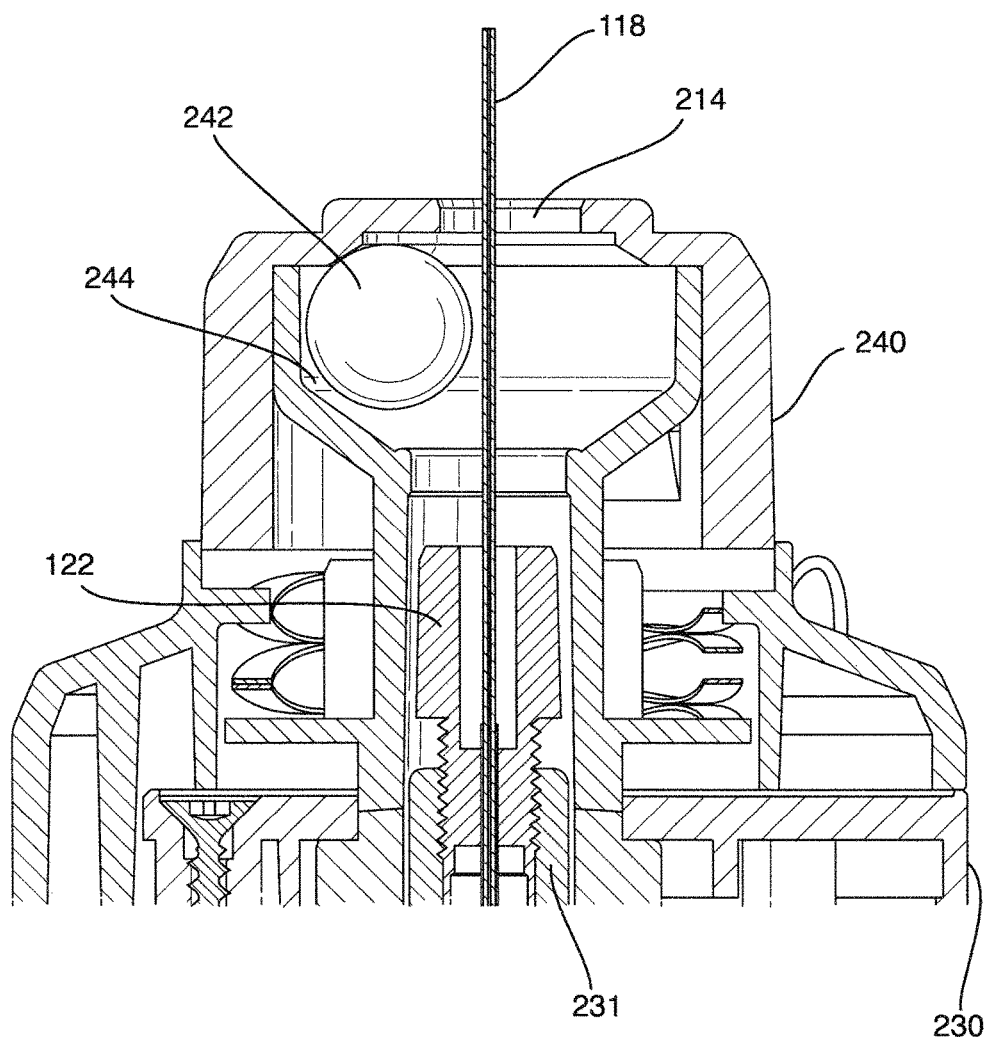
FIG. 17 shows schematically a cut away view of the cap and main adaptor body of the probe adaptor of FIGS. 5A and 5B when the probe assembly of FIG. 1 is installed in the adaptor.

As shown in FIGS. 13 and 17, the cap 240 is configured such that when the ball bearing 242 or other object is positioned within the one or more second pockets 244, and when the cap 240 is returned to or close to its upright position (e.g. when the cap 240 is secured to the main adaptor body 230), then the ball bearing 242 or other object will fall into the first pocket 243 when no probe assembly 110 is installed in the adaptor (when the probe assembly 110 is detached from the adaptor 200), or will not move into the first pocket 243, e.g. will substantially remain within the second pocket 244, when a probe assembly 110 is installed in the adaptor 200. For example, when the probe assembly 110 is inserted through the aperture 241, the line 118 of the probe assembly 110 may cause the ball bearing 242 or other object to remain within the second pocket 244.

It will accordingly be appreciated that the cap 240 is provided with a device for closing the aperture 241 and/or otherwise preventing access to the fitting 231 or its vicinity via the aperture 241 when the cap 240 is secured to the adaptor main body 230 and when a probe assembly 110 is not attached to the adaptor 200 (when the probe assembly 110 is detached from the adaptor 200). The device is configured such that when the aperture 241 is closed, the aperture 241 may be opened only when the cap 240 is removed from the adaptor main body 230 (i.e. when the cap 240 is opened). The device is, however, configured to remain open when a probe assembly 110 is installed in the adaptor 200 and the cap 240 is secured to the main adaptor body 230 (i.e. when the cap 240 is closed). The risk of electrical shock and/or contact with solvent, etc., to the user is therefore substantially reduced.

As described above, in some (e.g. ESI) embodiments, when the probe assembly 110 is installed in the adaptor 200, a portion of the outlet (downstream) end of the capillary 124 will extend beyond (downstream of) the probe tip 220, i.e. beyond (downstream of) the nebuliser gas capillary 221.

Figure 18:
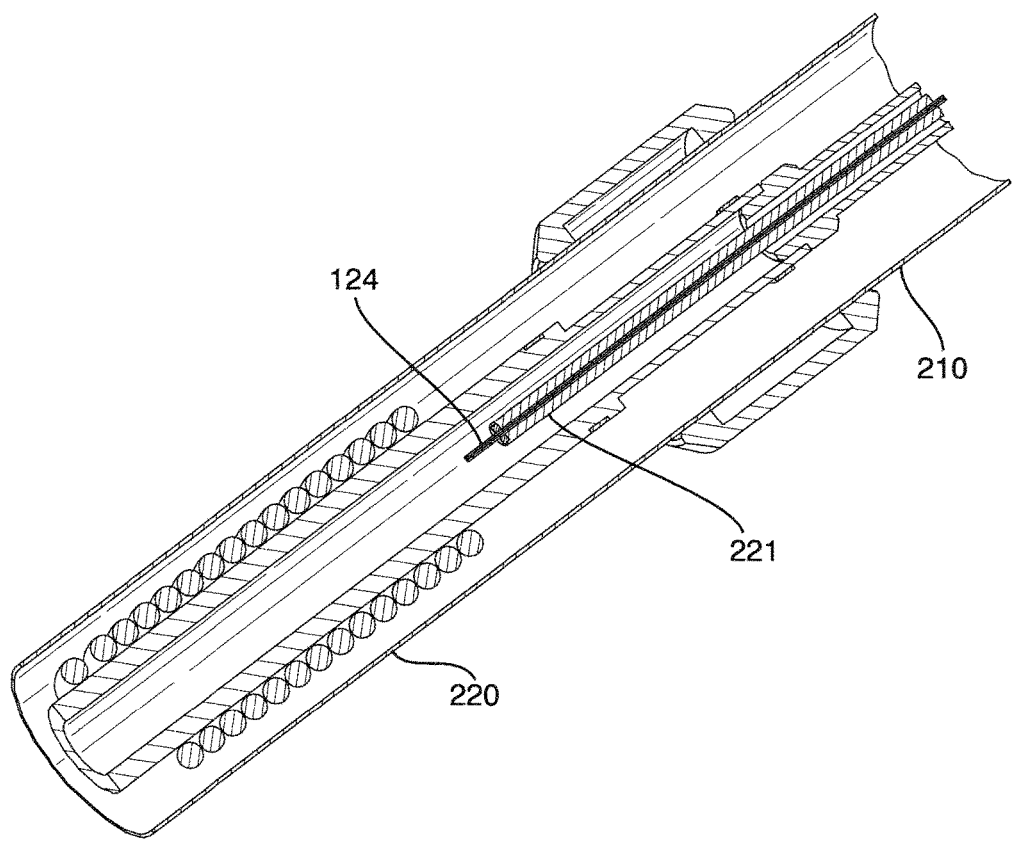
FIG. 18 shows schematically a cut away view of the adaptor of FIG. 6.

As illustrated in FIG. 18, in other (e.g. APCI) embodiments, when the probe assembly 110 is installed in the adaptor 200, a portion of the outlet (downstream) end of the capillary 124 will extend beyond (downstream of) the nebuliser gas capillary 221, but within the probe tip 220.

The position of the capillary 124 relative to the nebuliser gas capillary 221 is an important parameter that must be tightly controlled in order to optimise the ionisation process and/or in order to maintain a consistent ionisation process. For example, changes in the position of the outlet end of the capillary relative to the outlet end of the nebuliser gas capillary 221 can cause undesirable variations in the ionisation process.

As discussed above, in conventional arrangements, in order to remove the probe assembly 110 from the spectrometer, it is necessary to disassemble the probe tip 220. This necessarily means that the position of the outlet end of the capillary 124 relative to the outlet end of the nebuliser gas capillary 221 is lost. Thus, in conventional arrangements when a probe assembly 110 is removed and subsequently replaced, or when another probe assembly is installed in the spectrometer, the position of the outlet end of the capillary 124 relative to the outlet end of the nebuliser gas capillary 221 changes. The position must then be re-optimised or re-adjusted, thereby increasing downtime and cost for the spectrometer.

The adaptor 200 according to various embodiments described herein is provided with an adjustment mechanism that facilitates tool-free adjustment of the position of the outlet (downstream) end of the capillary 124 relative to the outlet (downstream) end of the nebuliser gas capillary 221. This means that the position of the outlet (downstream) end of the capillary 124 relative to the outlet (downstream) end of the nebuliser gas capillary 221 can be relatively easily and conveniently adjusted and/or optimised.

Furthermore, the adjustment mechanism according to various embodiments is configured such that when a probe assembly 110 is removed and subsequently replaced from the adaptor 200, or when another probe assembly 110 is installed in the adaptor 200, the position of the outlet (downstream) end of the capillary 124 relative to the outlet (downstream) end of the nebuliser gas capillary 221 substantially does not change, i.e. remains substantially fixed, or changes by a relatively small amount. This can reduce the amount of re-optimising or re-adjusting required, and may mean that the position does not need to be re-optimised or re-adjusted, thereby reducing downtime and cost associated with the spectrometer.

According to various embodiments, the adaptor 200 is provided with an adjustment mechanism or other control device for adjusting the position of the outlet (downstream) end of the capillary 124 relative to the outlet (downstream) end of the nebuliser gas capillary 221. As shown in FIG. 13 (and elsewhere), the adjustment mechanism may comprise a rotating dial 246 that is e.g. positioned on an external surface of the cap 240. This facilitates real-time optimising or adjustment of the distance, or "live tuning", e.g. during an experiment.

Rotation of the dial may cause the position of the outlet (downstream) end of the capillary 124 relative to the outlet (downstream) end of the nebuliser gas capillary 221 to change. The adaptor 200 may comprise any suitable mechanism in order to facilitate this, such as one or more cams, one or more lifting cams, and the like.

Figure 19:
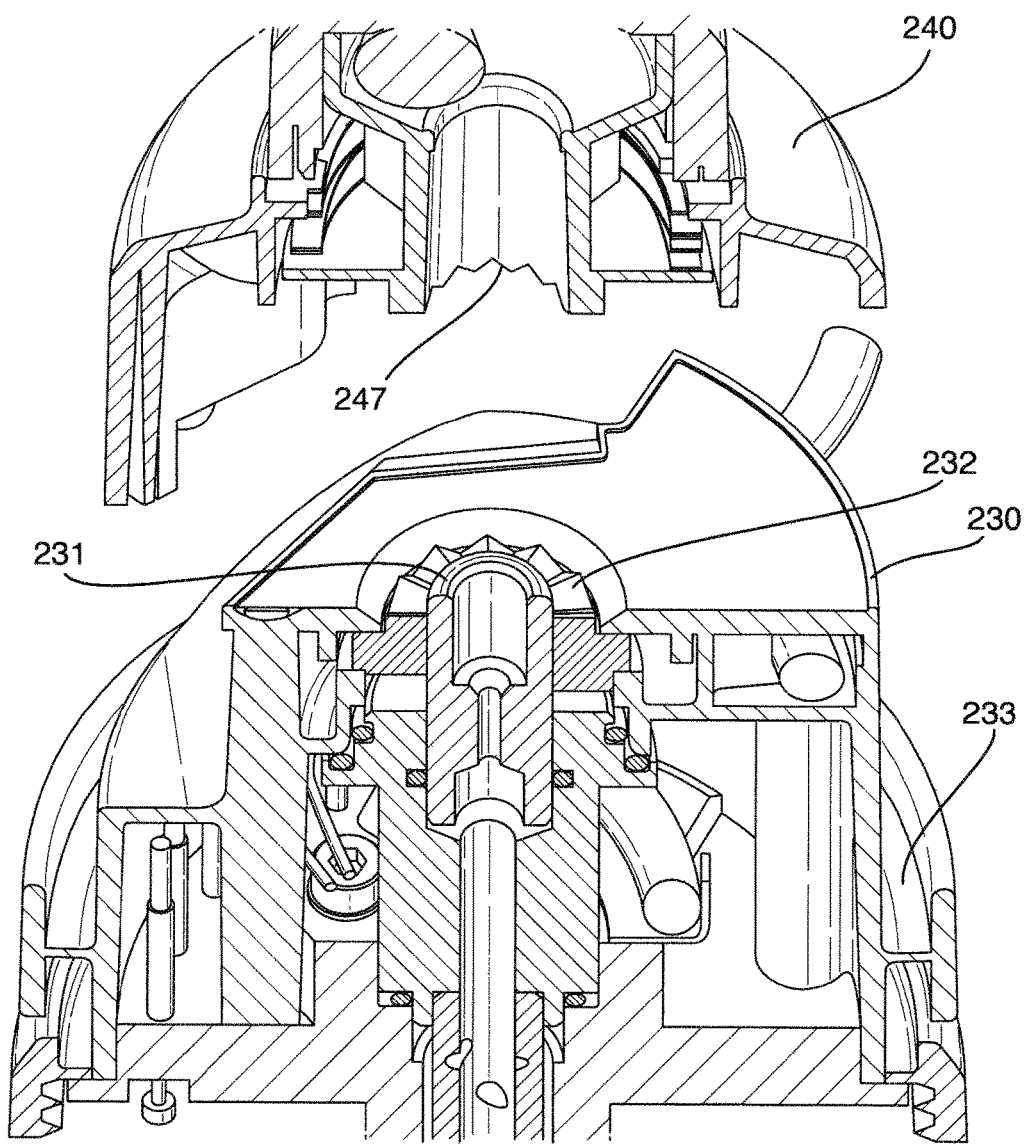
FIGS. 19, 20A, 20B, 20C, 21A, 21B, 22A and 22B show schematically a cut away views of the cap and main adaptor body of the probe adaptor of FIGS. 5A and 5B.

FIG. 19 shows a cut away detailed view of the cap 240 and the main adaptor body 230 in accordance with an embodiment. The rotating dial 246 may be connected to a first mechanism in the cap 240 that is configured to engage with a corresponding second mechanism in the adaptor main body 230, i.e. such that rotation of the dial 246 causes the second mechanism in the adaptor main body 230 to rotate (via rotation of the first mechanism in the cap 240) (when the cap 240 is secured to the main adaptor body 230).

For example, as shown in FIG. 19, the first mechanism may comprise a first set of teeth 247, and the second mechanism may comprise a corresponding second set of teeth 232. Each set of teeth may comprise plural teeth, e.g. having a circular arrangement that may be arranged to be coaxially aligned with the central longitudinal axis of the adaptor 200. In use, the first 247 and second 232 sets of teeth may face one another and may be configured so as to engage when the cap 240 is secured to the main adaptor body 230 (i.e. when the cap 240 is closed). Rotation of the dial 246 may cause the first set of teeth 247 to rotate, which in turn may cause the second set of teeth 232 to rotate (when the teeth are engaged, i.e. when the cap 240 is closed). Rotation of the second set of teeth 232 may cause the position of the outlet (downstream) end of the capillary 124 relative to the outlet (downstream) end of the nebuliser gas capillary 221 to be adjusted, e.g. via an appropriate mechanism (comprising one or more cams, one or more lifting cams, and the like) in the main adaptor body 230.

The dial 246 and/or the first set of teeth 247 may be continuously rotatable, i.e. the dial 246 and/or the first set of teeth 247 may have no preferred or "home" rotational position.

As such, rotation of the dial 246 may cause the position of the outlet (downstream) end of the capillary 124 relative to the outlet (downstream) end of the nebuliser gas capillary 221 to be adjusted. The dial 246 may be rotated without tools, and so this adjustment mechanism facilitates tool-free adjustment of the position of the outlet (downstream) end of the capillary 124 relative to the outlet (downstream) end of the nebuliser gas capillary 221.

Furthermore, the provision of plural engaging teeth in accordance with various embodiments means that when the teeth of the first 247 and second 232 sets of teeth are not aligned as the cap 240 is secured to the main adaptor body 230 (as the cap 240 is closed), then the rotational position of the second set of teeth 232 can only ever be altered by a maximum of half the pitch of the teeth when the cap 240 is secured to the main adaptor body 230, and so the position of the outlet (downstream) end of the capillary 124 relative to the outlet (downstream) end of the nebuliser gas capillary 221 will only ever be altered by a correspondingly small amount (that e.g. depends on the pitch of the teeth, and the pitch of the one or more cams or other devices to which the teeth are connected, and which may be selected as desired).

According to various further embodiments, one or both of the first 247 and second 232 sets of teeth may be spring loaded. That is, one or more springs or other elastic devices may be provided that are connected to the first 247 and/or second 232 sets of teeth. In this case, the first 247 and/or second 232 sets of teeth may be configured to be moveable, e.g. in the direction parallel to the central longitudinal axis of the orifice. The one or more springs or other elastic devices may be configured so as to be elastically deformed when the first 247 and/or second 232 sets of teeth are moved in this manner. This arrangement prevents the rotational position of the second set of teeth 232 from being altered (and therefore prevents the position of the outlet (downstream) end of the capillary 124 relative to the outlet (downstream) end of the nebuliser gas capillary 221 from being altered (at all)) when the first 247 and/or second 232 sets of teeth are brought into the engaged position when the teeth are not aligned.

In this case, rather than altering the rotational position of the second set of teeth 232 when the teeth are not aligned as the teeth are engaged, the longitudinal direction of the first 247 and/or second 232 set of teeth is instead altered, as the one or more springs or other elastic devices are deformed. Rotation of the first set of teeth 247 (due to rotation of the dial 246) will cause the teeth to become fully engaged as the two sets of teeth become properly aligned (and as the one or more springs or other elastic devices cause the first and/or second set of teeth to become fully engaged), without the rotational position of the second set of teeth 232 being altered.

This beneficially means that the teeth can be engaged with one another as the cap 240 is closed substantially without affecting the rotational position of the second set of teeth 232. This in turn means that when the cap 240 is opened and/or when a probe assembly 110 is removed from the adaptor 200 and is subsequently replaced, or when another probe assembly 110 is installed in the adaptor 200, the position of the outlet (downstream) end of the capillary 124 relative to the outlet (downstream) end of the nebuliser gas capillary 221 substantially does not change, i.e. remains substantially fixed.

This arrangement also facilitates real-time optimising or adjustment of the distance during an experiment, e.g., "live tuning".

Where the position of the outlet (downstream) end of the capillary 124 relative to the outlet (downstream) end of the nebuliser gas capillary 221 reaches a minimum or maximum, the provision of a spring loaded mechanism will also allow the first and/or second sets of teeth to then disengage, e.g. such that rotation of the dial 246 causes rotation of the first set of teeth 247, but not of the second set of teeth 132, i.e. as the first set of teeth 247 "ride" over the second set of teeth 132. An audible "clicking" sound when this occurs will alert a user to the fact that the position of the outlet (downstream) end of the capillary 124 relative to the outlet (downstream) end of the nebuliser gas capillary 221 has reached its minimum or maximum value. The surfaces of the teeth may be arranged to be resistant to wear.

FIGS. 20A, 20B, 20C, 21A, 21B, 22A and 22B illustrate the mechanism in more detail in accordance with an embodiment.

Figure 20A:
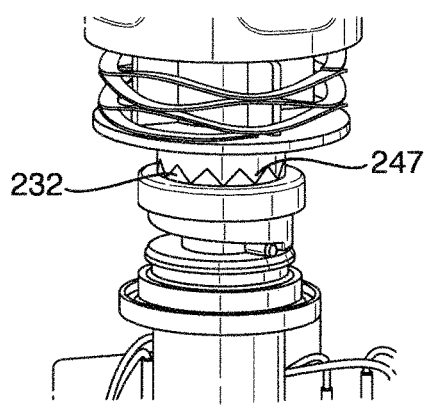
Figure 20B:
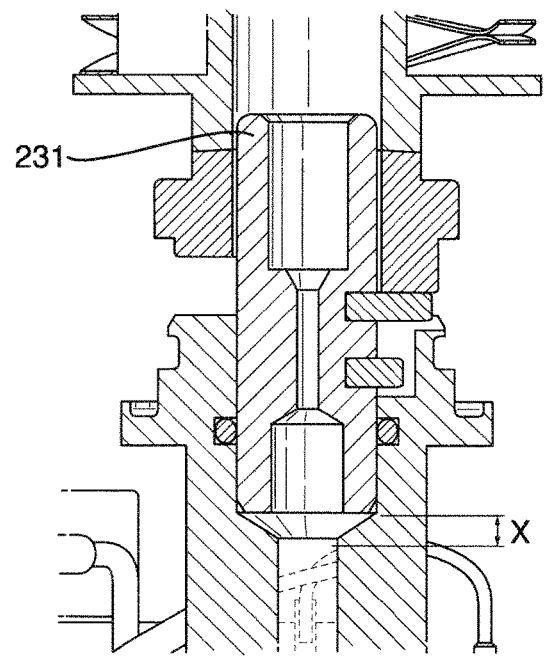
Figure 20C:
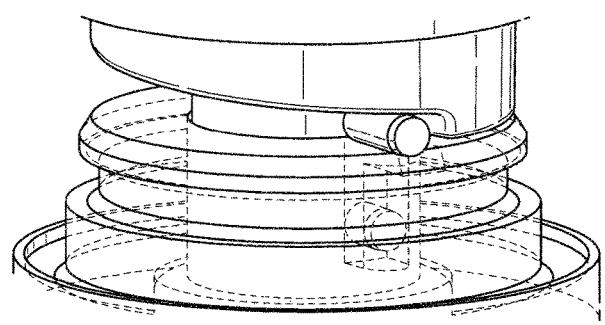
Figure 21A:
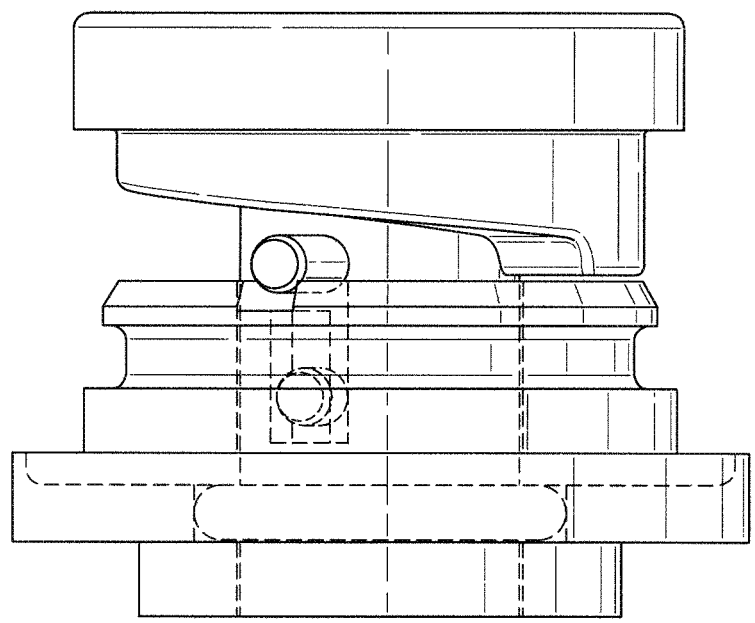
Figure 21B:
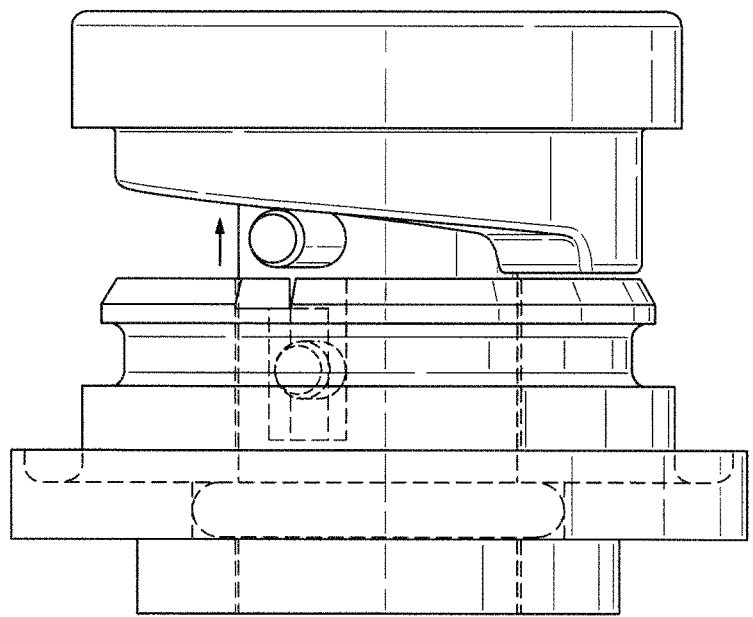
Figure 22A:
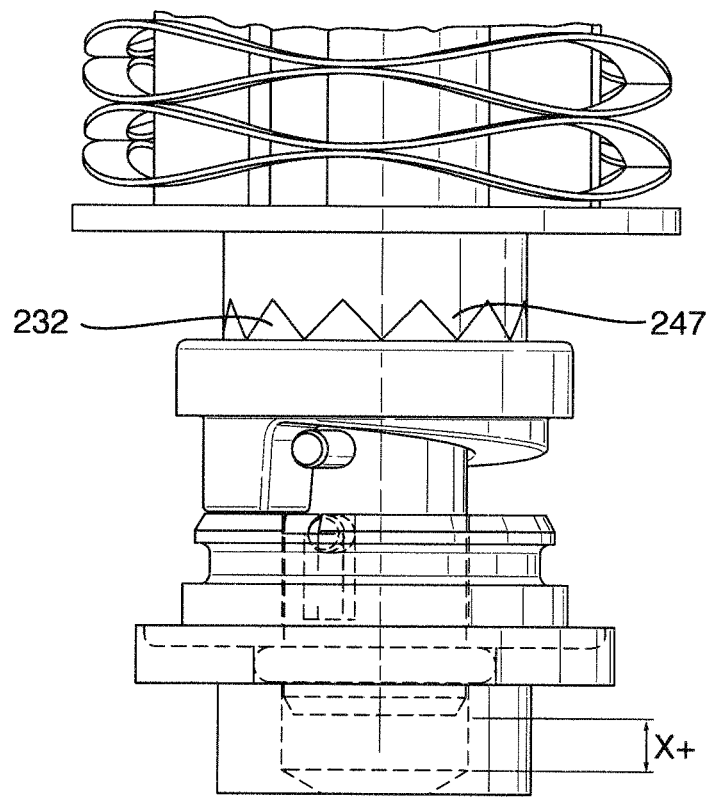
Figure 22B:
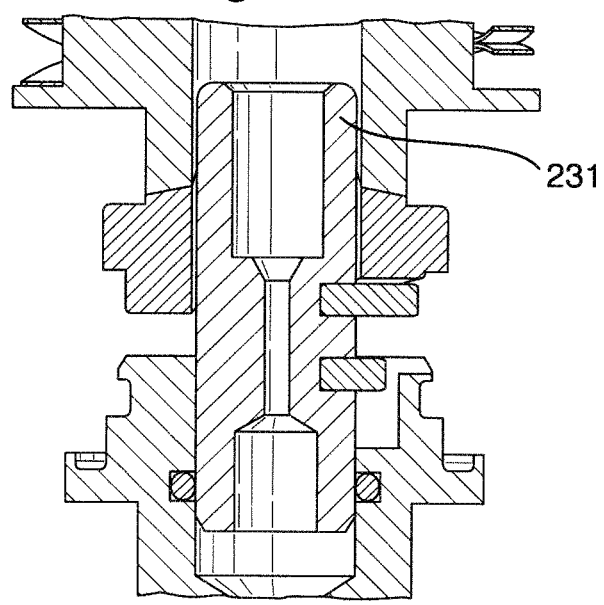

In this case, when the cap 240 is fitted to the main adaptor body 230, the two sets of teeth will turn together. As the teeth rotate, a cam slides along a dowel. The fitting 231 may be fixed (i.e. unable to rotate). FIGS. 20A, 20B and 20C illustrate the mechanism when it is in its lowest position (i.e. where the capillary 124 protrusion is greatest).

As the cam rotates, the gap from the bearing face of the dowel to the cam increases. This may be due to gas pressure from the ion source 310. The fitting 231 is pushed up (in the direction shown by the arrow in FIGS. 21A and 21B thereby increasing the distance "X". This decreases the capillary protrusion, i.e. because the probe, which has a fixed length, is fitted to the fitting 231.

According to various embodiments, the probe capillary does not rotate, but rather just moves in the axial "Z" direction, e.g. to a maximum "X+", e.g. up until the stop of the cam.

In some embodiments, one or two or more dowels may be provided and used, e.g. such that one is always in the slot.

Figure 23A:
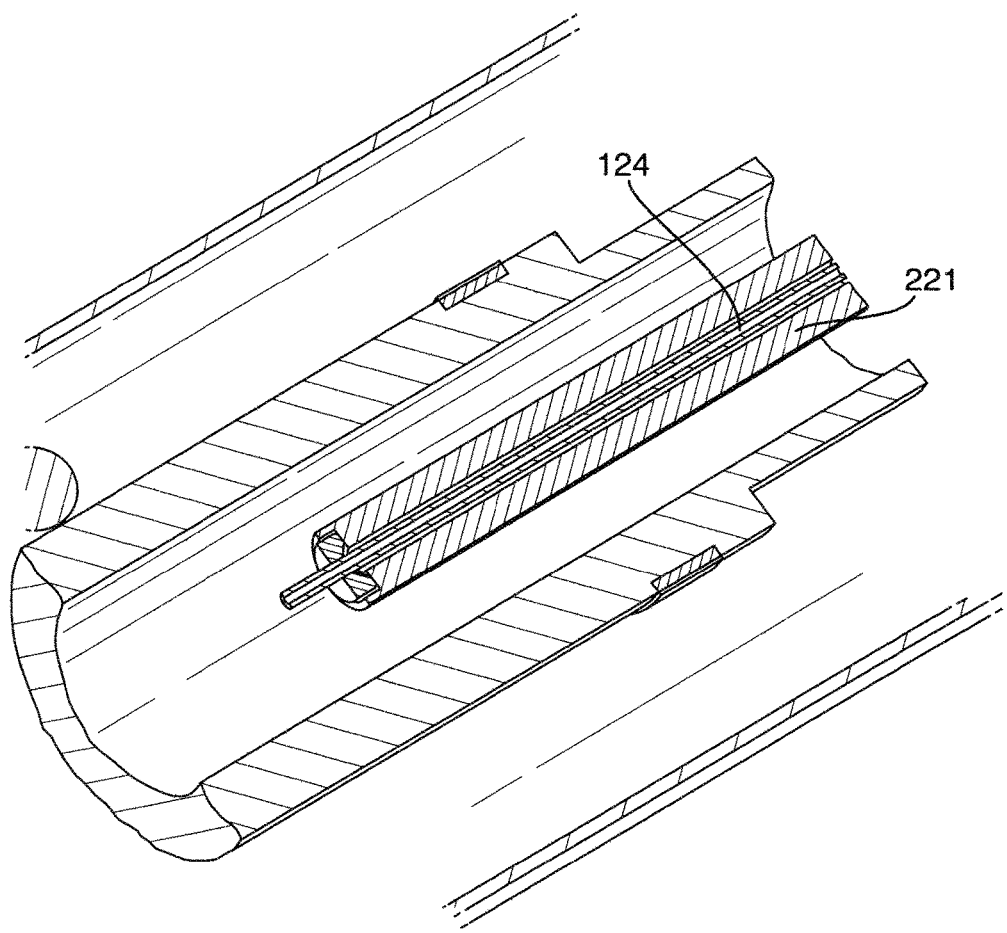
FIGS. 23A and 23B show schematically a cut away view of the adaptor of FIG. 6.
Figure 23B:
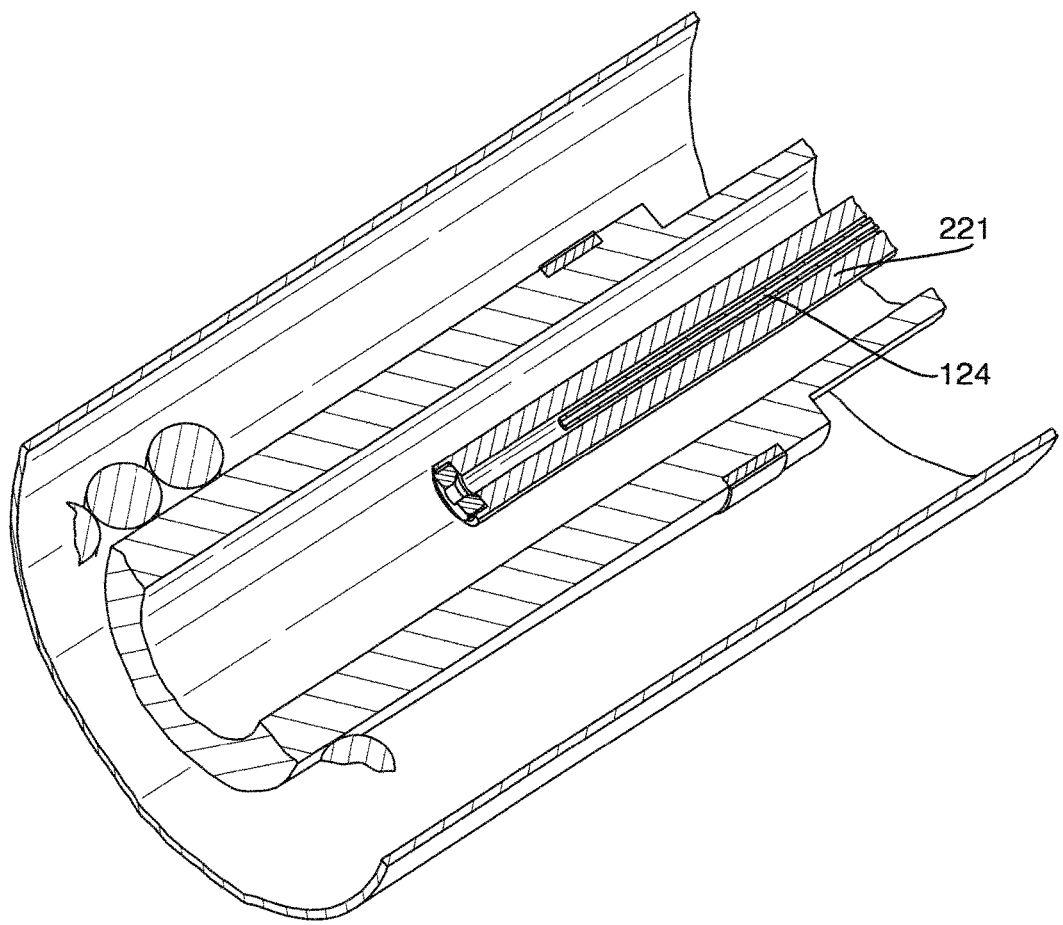

FIG. 23A shows the position of the outlet (downstream) end of the capillary 124 relative to the outlet (downstream) end of the nebuliser gas capillary 221 in a relatively extended position. FIG. 23B shows the position of the outlet (downstream) end of the capillary 124 relative to the outlet (downstream) end of the nebuliser gas capillary 221 in a relatively retracted position.

Figure 24A:
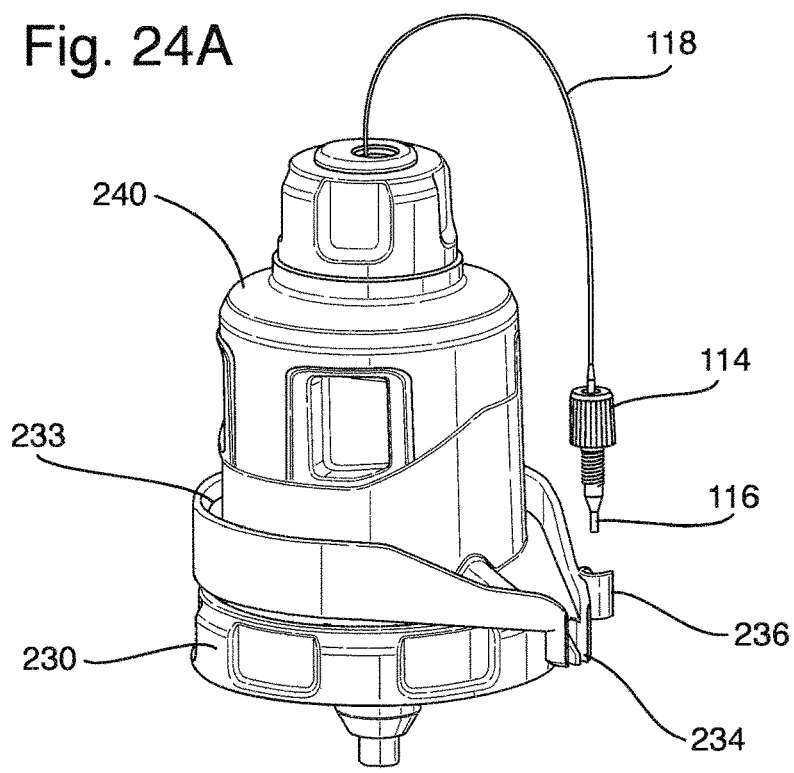
FIGS. 24A, 24B, and 24C show schematically the cap and main adaptor body of the probe adaptor of FIGS. 5A and 5B when the probe assembly of FIG. 1 is installed in the adaptor.
Figure 24B:
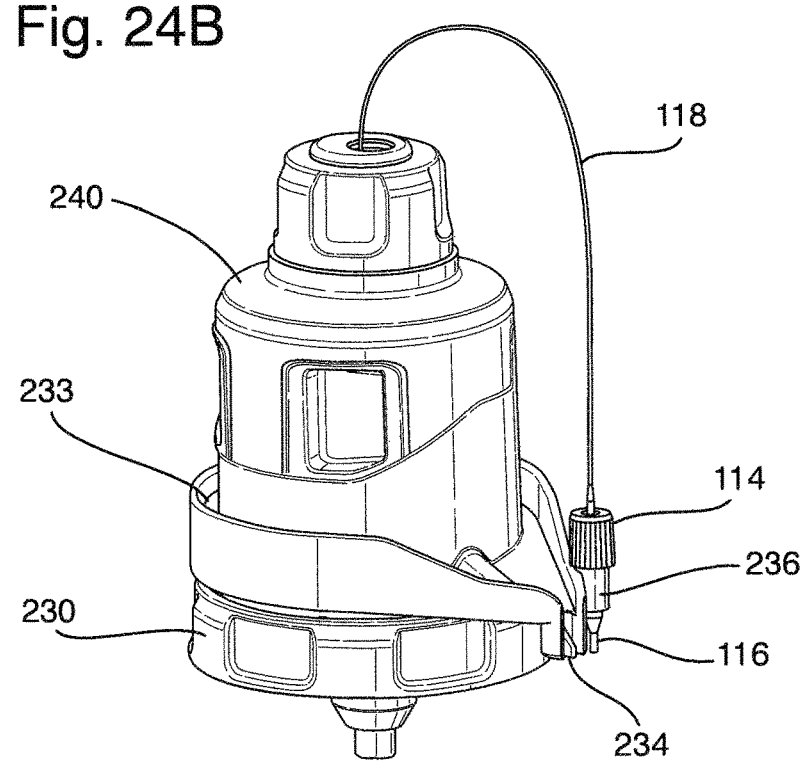
Figure 24C:
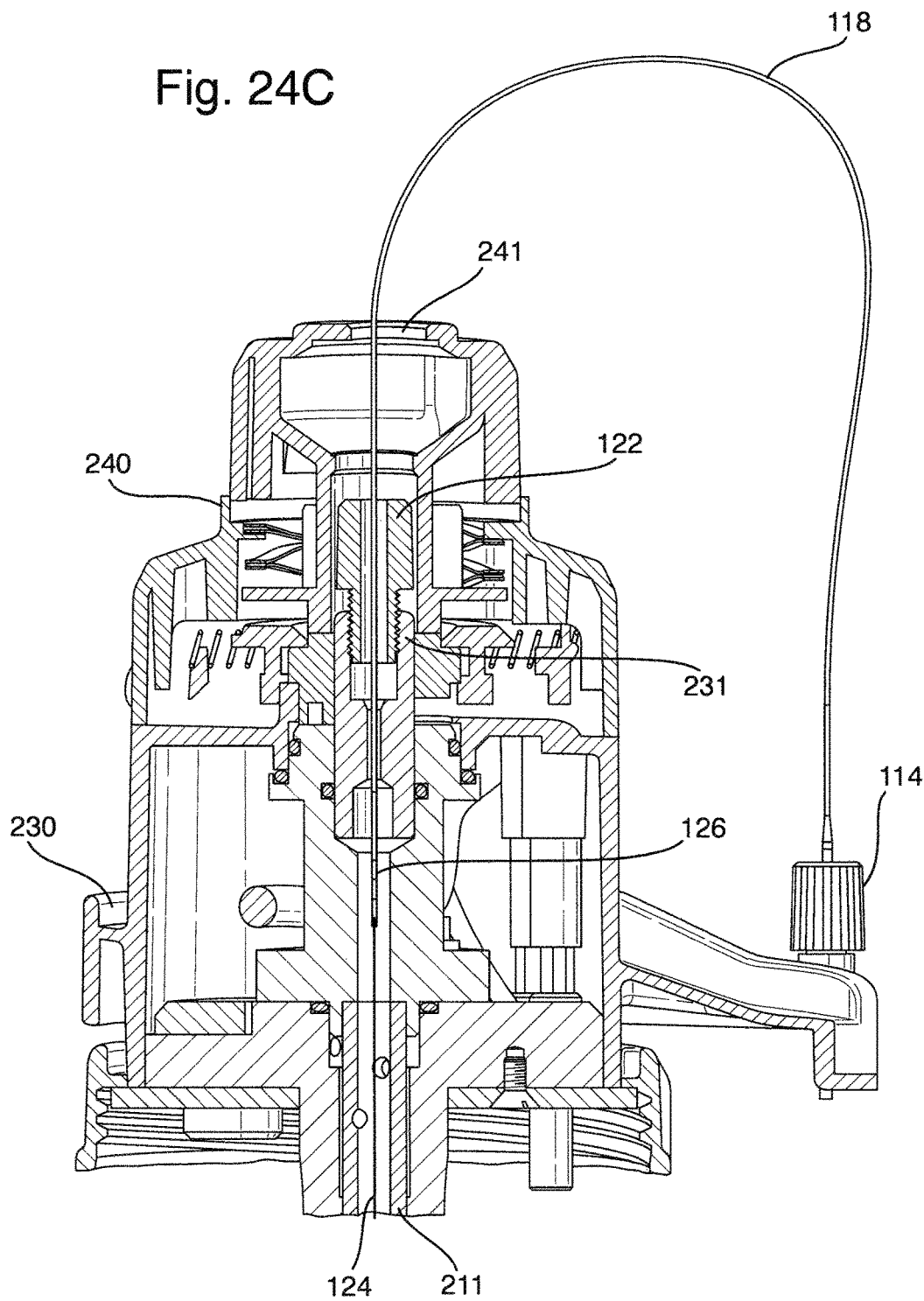

FIGS. 24A, 24B, and 24C show detailed views of the adaptor main body 230 and the cap 240 when a probe assembly 110 is installed in the adaptor 200 and when the cap 240 is closed, i.e. when the cap 240 is secured to the main adaptor body 230.

In use, the inlet end 112 of the probe assembly is attached to a chromatography device (not shown) (as described above).

The attachment device 114 at the inlet end 112 of the probe may be able to slide along the liquid line 118 and may be able to rotate about the liquid line 118. This allows the user to push the tube well into the supply fitting of the liquid chromatography device so as to reduce the dead volume. The attachment device 114 may then be rotated so as to screw it into the liquid chromatography device outlet and so as to make a seal therewith. Beneficially, this removes any need to twist the liquid line 118, which would otherwise stress the tube.

However, since the attachment relies on a user forming the attachment correctly, it is possible that a leak may develop between the chromatography device and the attachment device 114. In this case, it is possible that liquid may track along the liquid line 118 towards the adaptor 200. As discussed above, the presence of liquid gives rise to the risk of electrical shock and other risks to the user and/or to the instrument such as combustion of solvent, contact of liquid with electrical systems, and the user contacting solvent, etc. In addition, other liquid may be accidentally spilled on the adaptor, or otherwise (unintentionally) introduced to the adaptor.

In order to further address these problems, the adaptor main body 230 and/or cap 240 is configured such that liquid incident upon the adaptor main body 230 and/or the cap 240 will be directed away from the adaptor and/or probe interior. The adaptor main body 230 is provided with a liquid gutter or gully 233 which is arranged to collect liquid incident upon the adaptor main body 230 and/or the cap 240 and direct that fluid to a liquid drain or spout 234.

Figure 25A:
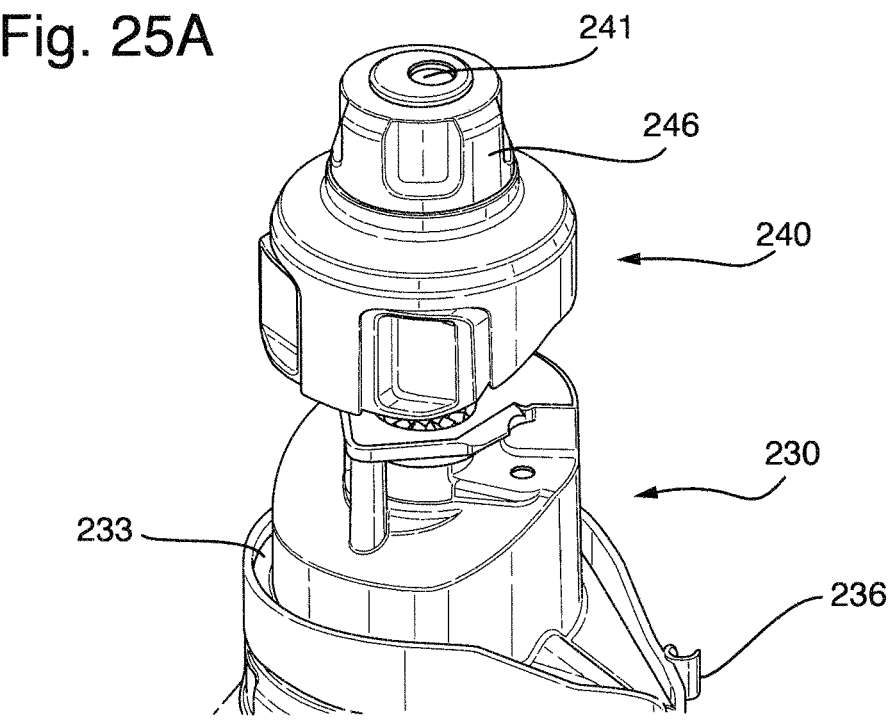
FIGS. 25A, 25B, and 25C show schematically the cap and main adaptor body of the probe adaptor of FIGS. 5A and 5B in more detail.
Figure 25B:
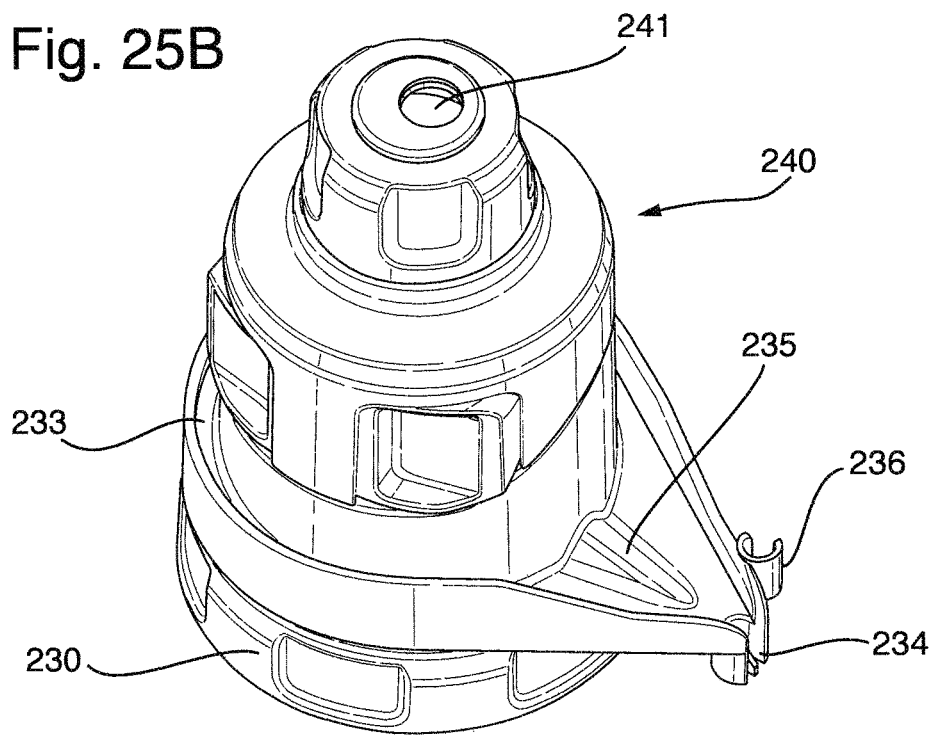
Figure 25C:
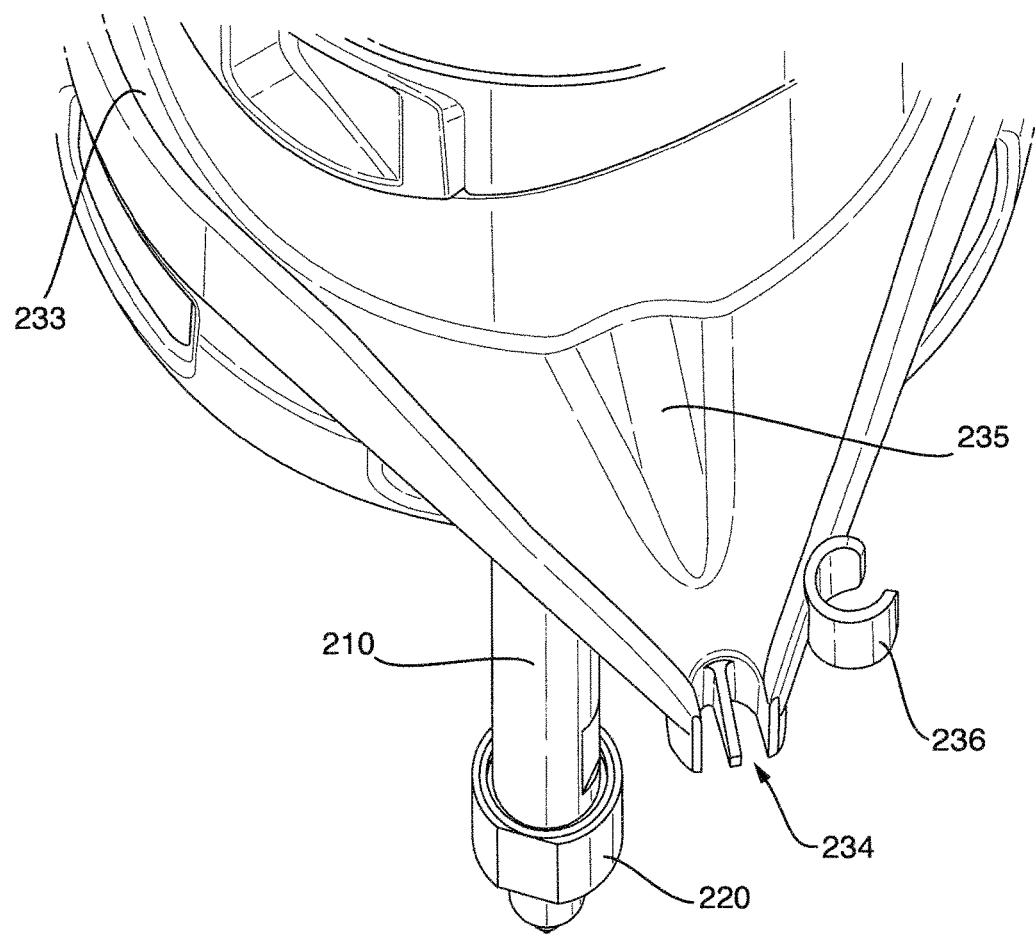

As shown in FIGS. 25A, 25B, and 25C, the gutter 233 is formed substantially continuously around the adaptor main body 230, e.g. 360 degrees around the sides of the adaptor 200, i.e. such that liquid incident upon most or all of the adaptor main body 230 and/or the cap 240 is collected by the gutter 233. The gutter 233 is configured such that collected liquid is directed to the liquid drain or spout 234, e.g. due to a sloping gutter floor.

The gutter 233 may be open-topped or otherwise arranged such that a user will be alerted to the presence of liquid in the gutter 233, e.g. by visual inspection, and thereby to the presence of a leak in the system.

The gutter 233 and/or drain 243 may be arranged so as to be fixed to the adaptor main body, e.g. such that the gutter 233 and/or drain 243 cannot be removed, e.g. when a user installs a probe into the adaptor 200.

The drain 234 is arranged such that the liquid collected by the gutter 233 will drip or otherwise fall from the drain 234. By arranging for the liquid to drip in this way, a continuous electrical conduction path cannot be formed by the unwanted liquid, thereby reducing the risk of electrical shock.

The drain 234 may be arranged such that the drain maintains a fixed position, e.g. relative to the adaptor 200. Accordingly, liquid collected by the gutter 233 will drip or otherwise fall in a position selected by a user.

According to various embodiments, the drain 234 comprises one or more (open-ended) slots or other indentations. In use, the liquid drips via the one or more slots or other indentations. This is beneficial, e.g. when compared to a drain comprising an aperture or hole, since the provision of one or more open ended slots or other indentations means that there is no possibility of the drain becoming blocked, e.g. due to high viscosity liquid, distilled components, etc. blocking the aperture or hole.

As shown in FIG. 25C, a portion of the gutter 233 that is in proximity with the drain 234 may comprise a relatively wide channel region that is configured to direct liquid collected in the gutter 233 to the liquid drain 234, e.g. due to a sloping floor. According to various embodiments, the channel region may be provided with a fin, bump, ridge or other protrusion 235.

Figure 26A:
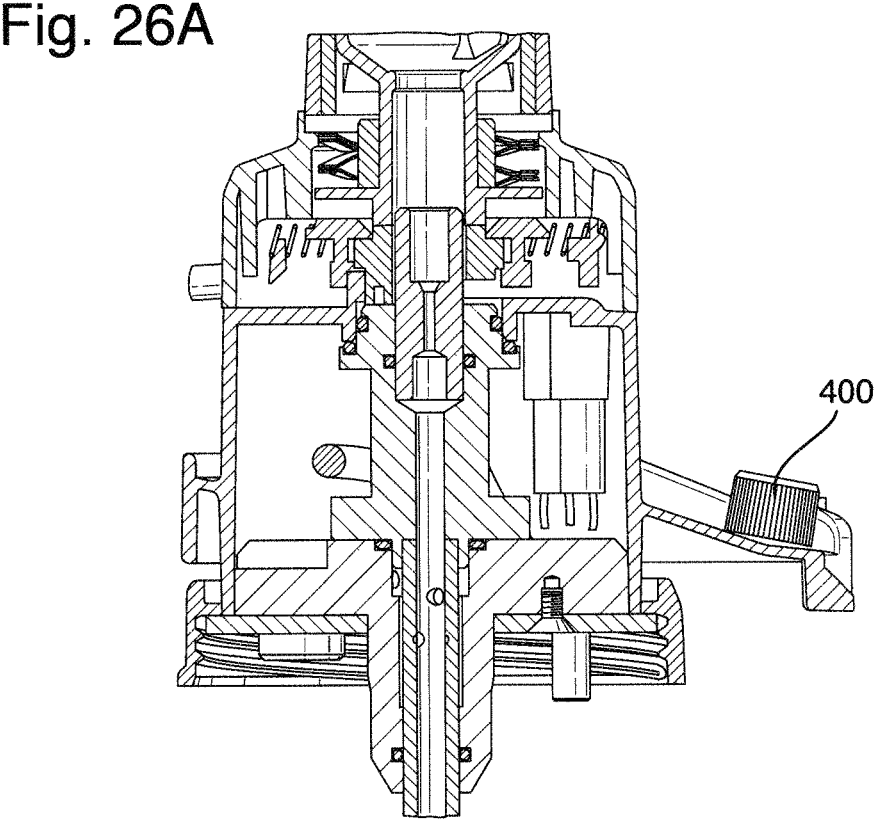
FIGS. 26A and 26B show schematically the cap and main adaptor body of the probe adaptor of FIGS. 5A and 5B when an object is inserted into the gutter.
Figure 26B:
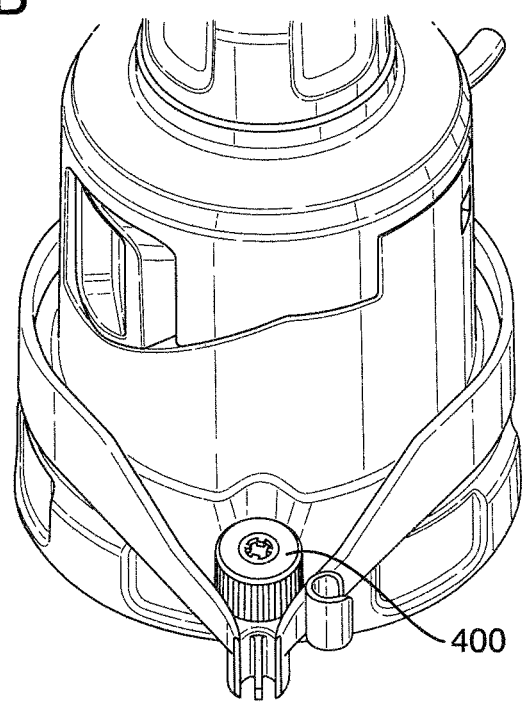

As illustrated by FIGS. 26A and 26B, the fin, bump, ridge or other protrusion 235 is arranged so as to reduce the possibility of the channel region and/or drain 234 becoming blocked, e.g. by a foreign object 400 being placed in the channel region and/or drain 234 region. In particular, the fin, bump, ridge or other protrusion 235 may be arranged such that a flat surface seal cannot or is less likely to form between a foreign object 400 and the channel region and/or drain 234 region. In particular, the fin or other protrusion 235 may be arranged such that the channel region and/or drain 234 cannot be blocked by the inlet end 112 of the probe assembly 110, a cap or other fitting.

According to various embodiments, the adaptor main body 230 is also provided with a device 236 for holding the inlet end 112 of the probe assembly 110, i.e. when not in use, e.g. a "parking space" for the inlet end 112 of the probe assembly 110. This beneficially encourages the user to avoid using the gutter 233 to hold the inlet end 112 of the probe assembly, which may cause blockages.

Figure 27A:
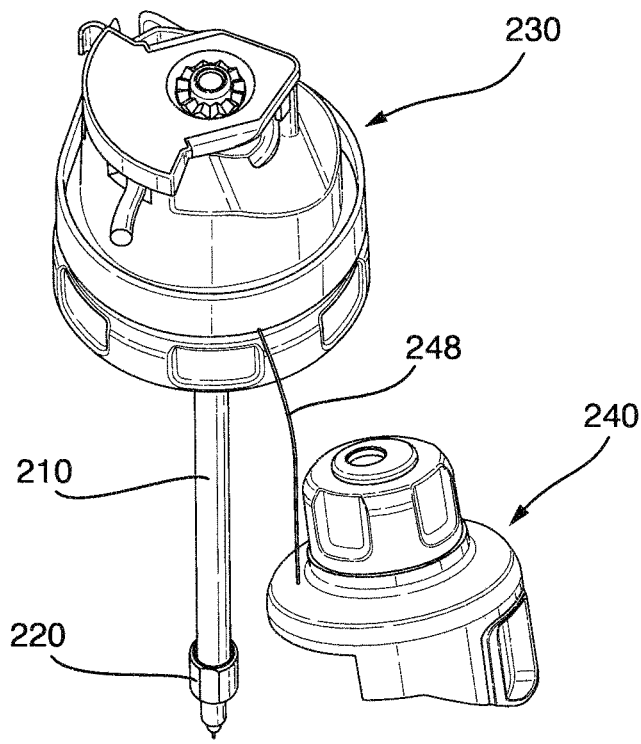
FIGS. 27A and 27B shows schematically the cap and main adaptor body of the probe adaptor of FIGS. 5A and 5B when the cap is opened.
Figure 27B:
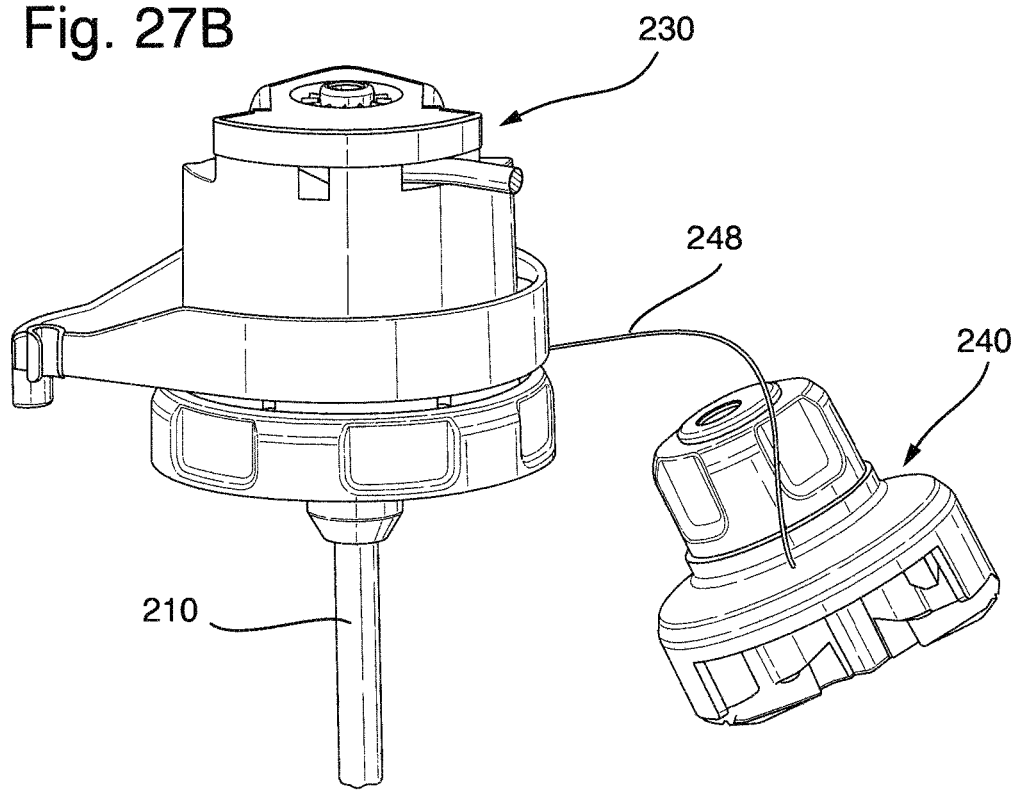

According to various embodiments, the cap may be attached to the main body 230, e.g. by a cord, hinge, or other means. For example, as shown in FIGS. 27A and 27B, the cap 240 may be attached to the adaptor main body 230 by a cord or lanyard 248. This beneficially prevents the cap from being lost. This also simplifies the process of removing/installing a probe assembly in the adaptor 200 since, for example, it is not necessary for a user to keep hold of the cap 240.

According to an embodiment, the cap 240 and/or main adaptor body 230 comprises one or more asymmetric mating portions, e.g. such that the cap 240 can be secured to the main adaptor body 230 (i.e. can be closed) only in one (correct) orientation and/or position.

According to an embodiment, the cap 240 and/or main adaptor body 230 is configured so as to produce one or more audible clicks when the cap 240 is fitted securely to the main adaptor body 230.

According to an embodiment, the cap 240 is configured such that tools are not required in order to open the cap 240 (to remove the cap 240 from the main adaptor body 230). The cap 240 may comprise one or more buttons, configured such that when the button(s) are pushed, the cap 240 is opened.

In particular, the cap 240 may comprise two buttons or flippers, configured such that when the buttons are pushed together, the cap 240 is opened. The two buttons or flippers may be arranged such that a user must deliberately intend to open the cap 240 in order for the cap to be opened. For example, the two buttons may be configured such that a pinching action is required in order to open the cap 240. It would also be possible to provide more buttons or flippers, e.g. three or more, that must simultaneously be operated or otherwise to open the cap 240.

The one or more buttons may be configured such that the cap can be opened and removed in one motion. The cap may be configured such that the cap may be opened whether a probe assembly is installed or not.

The cap 240 may be provided with one or more springs or other elastic devices configured such that when the cap 240 is opened, the cap 240 is ejected from the main adaptor body 230.

Although various embodiments have been described for use in an electrospray ion source, it may be used in other types of ion source such as an atmospheric pressure chemical ionisation source (APCI) or an impactor spray ion source.

Although the above embodiments have been described primarily in terms of a probe adaptor assembly, it would also or instead be possible for one or more of all of the components of the adaptor to be integrated with the ion source and/or the spectrometer.

Although the present invention has been described with reference to preferred embodiments, it will be understood by those skilled in the art that various changes in form and detail may be made without departing from the scope of the invention as set forth in the accompanying claims.

The invention claimed is:

1. Apparatus for connecting an ionisation probe assembly to a mass and/or ion mobility spectrometer, the apparatus comprising:
   an attachment member for releasably attaching a probe assembly to the apparatus; and
   a cap for enclosing the attachment member, the cap comprising an aperture through which at least a portion of the probe assembly can pass;
   wherein the cap is configurable to enclose the attachment member when a probe assembly is attached to the apparatus; and
   wherein the apparatus comprises a device configured to close the aperture when the cap is arranged to enclose the attachment member and when no probe assembly is attached to the apparatus.

2. The apparatus of claim 1, wherein the cap is configurable to enclose the attachment member when no probe assembly is attached to the apparatus so as to prevent a probe assembly being brought into contact with the attachment member.

3. The apparatus of claim 1, wherein the device is configured such that the aperture is openable, in use, only when the attachment member is not enclosed by the cap.

4. The apparatus of claim 1, wherein the device comprises one or more balls or other objects and one or more pockets for receiving the one or more balls or other objects.

5. The apparatus of claim 4, wherein the one or more balls or other objects have a size and/or shape such that the one or more balls or other objects cannot pass through the aperture.

6. The apparatus of claim 4, wherein the one or more balls or other objects have a diameter greater than the diameter of the aperture.

7. The apparatus of claim 4, wherein the one or more pockets comprise at least a first pocket for receiving the one or more balls or other objects, and wherein the cap is configured such that, when the cap is in an upright position, the one or more balls or other objects will fall into the first pocket.

8. The apparatus of claim 7, wherein the one or more pockets further comprise one or more second pockets, and wherein the cap is configured such that, when the cap is in a horizontal position, the one or more balls or other objects will fall into the one or more second pockets.

9. The apparatus of claim 8, wherein the one or more second pockets comprise a single pocket that extends in a loop around the aperture.

10. An adaptor for connecting an ionisation probe assembly to a mass and/or ion mobility spectrometer, the adaptor comprising apparatus as claimed in claim 1.

11. A mass and/or ion mobility spectrometer comprising apparatus as claimed in claim 1.

12. A method of delivering eluent to a mass and/or ion mobility spectrometer comprising:
   providing a probe assembly;
   providing apparatus as claimed in claim 1;
   releasably attaching the probe assembly to the apparatus using the attachment member; and
   supplying eluent to the probe assembly such that eluent is transmitted through the probe assembly into the spectrometer.

13. Apparatus for connecting an ionisation probe assembly to a mass and/or ion mobility spectrometer, the apparatus comprising:
   an attachment member for releasably attaching a probe assembly to the apparatus; and
   a probe tip configured to receive a capillary of the probe assembly;
   wherein the apparatus is configured such that the position of the capillary relative to the probe tip remains substantially unaltered when a probe assembly is detached from and/or attached to the apparatus.

14. The apparatus of claim 13, wherein:
   the probe tip comprises a capillary configured to receive the capillary of the probe assembly; and
   the apparatus is configured such that the position of the capillary relative to the probe tip capillary remains substantially unaltered when a probe assembly is detached from and/or attached to the apparatus.

15. The apparatus of claim 14, wherein:
   the apparatus further comprises a cap for enclosing the attachment member;
   the attachment member is provided in a main body of the apparatus; and
   the cap is releasably securable to the main body so as to enclose the attachment member.

16. The apparatus of claim 15, wherein:
   the cap comprises a first mechanism that is engageable with a second mechanism in the main body; and
   the first and/or second mechanisms are configured such that the position of the capillary relative to the probe tip remains substantially unaltered when the cap is secured to and/or released from the main body.

17. The apparatus of claim 16, wherein:
   the cap further comprises one or more springs or other elastic devices that are connected to the first and/or second mechanisms;
   wherein the one or more springs or other elastic devices are configured so as to be elastically deformed when the first and/or second mechanisms are moved.

18. Apparatus for connecting an ionisation probe assembly to a mass and/or ion mobility spectrometer, the apparatus comprising:

an attachment member for releasably attaching a probe assembly to the apparatus; and a cap for enclosing the attachment member, the cap comprising two or more buttons or flippers;

wherein the two or more buttons or flippers are configured such that when the buttons or flippers are pushed together, the cap is opened.

19. The apparatus of claim 18, wherein the two or more buttons or flippers are configured such that a pinching action is required in order to open the cap.

20. The apparatus of claim 18, wherein the cap further comprises one or more springs or elastic devices, wherein the one or more springs or elastic devices are configured such that when the cap is opened, the cap is ejected from the apparatus.

* * * * *